United States Patent [19]

Douglas et al.

[11] Patent Number: 4,488,993
[45] Date of Patent: Dec. 18, 1984

[54] AMIDINOUREAS

[75] Inventors: George H. Douglas, Paoli; Julius Diamond, Lafayette Hill, both of Pa.

[73] Assignee: William H. Rorer, Inc., Fort Washington, PA 19034

[21] Appl. No.: 436,490

[22] Filed: Oct. 25, 1982

Related U.S. Application Data

[60] Continuation of Ser. No. 178,426, Aug. 15, 1980, abandoned, which is a division of Ser. No. 925,145, Jul. 17, 1978, Pat. No. 4,220,658, which is a continuation of Ser. No. 805,371, Jun. 10, 1977, abandoned, which is a continuation of Ser. No. 687,266, May 17, 1976, abandoned, which is a continuation of Ser. No. 385,797, Aug. 6, 1973, abandoned, which is a continuation-in-part of Ser. No. 291,474, Sep. 22, 1972, abandoned.

[51] Int. Cl.³ .................. C07C 127/19; C07D 205/06
[52] U.S. Cl. ................ 260/239 A; 260/239 B; 544/165; 544/400; 546/226; 548/188; 564/47; 564/48; 564/49; 564/50; 564/52; 564/53; 424/322
[58] Field of Search ............ 564/47, 48, 49, 50, 564/52, 53, 54; 424/322; 260/239 B, 239 A; 544/165, 400; 546/226; 548/188

[56] References Cited

U.S. PATENT DOCUMENTS

| | | | |
|---|---|---|---|
| 2,631,152 | 3/1953 | Ritter et al. | 564/47 X |
| 3,320,229 | 5/1967 | Szabo et al. | 260/553 R X |
| 3,539,616 | 11/1970 | Walls | 260/553 A X |
| 4,025,652 | 5/1977 | Diamond et al. | 564/47 |
| 4,058,557 | 11/1977 | Douglas et al. | 260/553 A X |
| 4,060,635 | 11/1977 | Diamond et al. | 260/553 A X |
| 4,203,920 | 5/1980 | Diamond et al. | 260/553 A |
| 4,204,000 | 5/1980 | Diamond et al. | 260/553 A X |
| 4,220,658 | 9/1980 | Douglas et al. | 564/47 X |
| 4,326,074 | 4/1982 | Diamond et al. | 564/47 |
| 4,340,609 | 7/1982 | Chou | 424/322 |

FOREIGN PATENT DOCUMENTS

| | | |
|---|---|---|
| 2345951 | 4/1974 | Fed. Rep. of Germany. |
| 7313040 | 3/1974 | Netherlands. |

*Primary Examiner*—Thomas A. Waltz
*Attorney, Agent, or Firm*—James A. Nicholson; John C. Smith, Jr.

[57] ABSTRACT

Novel phenylamidinourea compounds and processes for their preparation are described. These compounds have an effective degree of anti-hypertensive properties and exert activities on the cardiovascular system. A method for the treatment of hypertensive disorders is also described.

2 Claims, No Drawings

AMIDINOUREAS

CROSS REFERENCE TO RELATED APPLICATIONS

This is a continuation of copending application Ser. No. 178,426 filed Aug. 15, 1980 (now abandoned) which is a division of copending application Ser. No. 925,145 filed July 17, 1978 (now U.S. Pat. No. 4,220,658) which is a continuation of application Ser. No. 805,371 filed June 10, 1977 (now abandoned) which is a continuation of Ser. No. 687,266 filed May 17, 1976 (now abandoned) which is a continuation of Ser. No. 385,797 filed Aug. 6, 1973 (now abandoned) which is a continuation-in-part of Ser. No. 291,474, filed Sept. 22, 1972, now abandoned.

SUMMARY OF THE INVENTION

This invention describes new substituted phenylamidinourea compounds and processes for their preparation. This invention further provides valuable pharmaceutical preparations which contain substituted phenylamidinourea compounds which possess an effective degree of antihypertensive properties and exert activities on the cardiovascular system. A method for the treatment of hypertensive disorders by the administration of a substituted phenylamidinourea compound is also described.

BACKGROUND OF THE INVENTION

The pharmaceutical compositions which have been used as antihypertensive agents have included such as the thiazides, reserpine, hydralazine, α-methyl dopa, guanethidine and the like. These compounds, however, while being effective produce undesirable side effects such as electrolyte imbalance, orthostatic hypertension, and gastric secretory and spasmolytic properties.

We have unexpectedly found that amidinourea compounds exhibit valuable pharmacologic properties.

We have unexpectedly found that the amidinoureas of this invention are useful antihypertensive agents.

We have further found that the amidinourea compounds of this invention are novel and can easily be prepared.

We have also found that the compounds of this invention have a minimum of the side effects which accompany antihypertensive agents.

We have still further found a simple and effective method for the treatment of cardiovascular disorders such as hypertensive disorders.

DESCRIPTION AND PREFERRED EMBODIMENT

This invention describes a class of novel chemical compounds which comprises a substituted phenyl radical which is further attached to a substituted amidinourea chain. This results in urea and substituted urea type compounds having a phenylamidino or a substituted phenylamidino group attached at one of the nitrogen atoms. This invention also describes the non-toxic pharmaceutically acceptable salts and the method of preparing these substituted phenylamidinourea compounds.

The novel compounds of this invention are described by the structural formula I

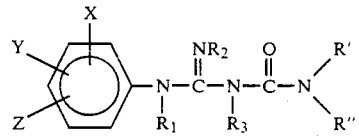

where:
X is hydrogen, loweralkyl, halo;
Y is hydrogen, halo, haloloweralkyl, nitro, loweralkyl or loweralkoxy;
Z is halo, loweralkoxy, loweralkyl, nitro, cyano, haloloweralkyl, haloloweralkoxy o, loweralkylsulfonyl;
$R_1$, $R_2$ and $R_3$ are hydrogen or loweralkyl;
R' and R" are hydrogen, loweralkyl, intermediate alkyl, loweralkenyl, cycloalkyl, cycloalkylloweralkyl, aralkyl, cycloalkenyl or
R' and R" together are loweralkylidenyl or heteroloweralkylidenyl, provided $R_1$, $R_2$, $R_3$, R' and R" are not all hydrogen at the same time; and
the non-toxic acid addition salts thereof.

Compounds of this invention which are preferred are described by general formula I where:
X is hydrogen or loweralkyl, halo;
Y is hydrogen, halo, loweralkyl or haloloweralkyl; and
Z is halo, loweralkyl or loweralkoxy, nitro, haloloweralkyl;
$R_1$, $R_2$ and $R_3$ are hydrogen or loweralkyl; and
R' and R" are hydrogen, loweralkyl or cycloalkyl;
provided $R_1$, $R_2$, R' and R" are not all hydrogen at the same time.

The more preferred compounds of this invention include those compounds where:
X is hydrogen, methyl, ethyl, propyl, i-propyl, butyl, chloro, bromo or fluoro;
Y is hydrogen, chloro, bromo, fluoro, methyl, ethyl, propyl, i-propyl, butyl, trifluoromethyl; and
Z is chloro, bromo, fluoro, methyl, ethyl, propyl, i-propyl, butyl, methoxy, ethoxy, nitro or trifluoromethyl;
$R_1$, $R_2$ and $R_3$ are hydrogen, methyl or ethyl;
R' and R" are hydrogen, methyl, ethyl, propyl, i-propyl, butyl, t-butyl, cyclopropyl, cyclobutyl, cyclopentyl or cyclohexyl;
provided $R_1$, $R_2$, $R_3$, R' and R" are not all hydrogen at the same time.

The most preferred compounds of this invention are described where:
X is hydrogen, chloro, bromo, fluoro, methyl or ethyl;
Y is hydrogen, chloro, bromo, fluoro, methyl, ethyl or trifluoromethyl;
Z is chloro, bromo, fluoro, methyl, ethyl or trifluoromethyl;
$R_1$, $R_2$ and $R_3$ are hydrogen or methyl; and
R' and R" are hydrogen, methyl, ethyl, propyl, i-propyl, butyl or t-butyl;
provided $R_1$, $R_2$, $R_3$, R' and R" are not all hydrogen at the same time.

A special embodiment of this invention is described where X is hydrogen, Y is 2-chloro and Z is 6-chloro.

Another special embodiment is described where X and Y are hydrogen and Z is 4-fluoro.

A further special embodiment is described where X is 2-methyl or 2-ethyl; Y is hydrogen; and Z is in the 6-position and is chloro, bromo, fluoro, methyl or ethyl.

Another special embodimetn is described where X is in the 6-position and is chloro, bromo or fluoro; Y is in the 4-position and is methyl, ethyl, chloro, bromo or fluoro; and Z is in the 2-position and is chloro, bromo or fluoro.

A further embodiment is described where X is 2-methyl or 2-ethyl; Y is in the 4-position and is methyl, ethyl, chloro, bromo or fluoro; and Z is in the 6-position and is methyl, ethyl, chloro, bromo or fluoro.

In the descriptive portions of this invention, the following definitions apply:

The nomenclature applied to the compounds of this invention

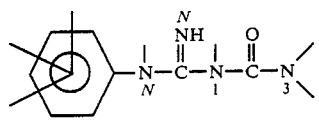

The term "loweralkyl" refers to an alkyl hydrocarbon group containing from 1 to 5 carbon atoms which may be straight chained or branched.

The term "intermediate alkyl" refers to an alkyl hydrocarbon group containing from 6 to 12 carbon atoms which may be straight chained or branched.

The "acyl" radical may be any organic radical derived from an organic acid by its removal of the hydroxy group such as benzoyl, toluyl, etc.

The "loweralkoxy" radical signifies an alkoxy group containing from 1 to about 6 carbon atoms which can be straight chained or branched.

The "loweralkenyl" group refers to an alkenyl hydrocarbon group containing from 2 to about 6 carbon atoms which may be straight chained or branched.

"Cycloalkyl" refers to a cycloalkyl hydrocarbon ring having from 3 to 8 carbon atoms.

"Cycloalkenyl" refers to a cycloalkenyl hydrocarbon ring having from 3 to 8 carbon atoms.

The "loweralkylidenyl" radical refers to an alkylidene hydrocarbon radical containing from 2 to 8 carbon atoms thus forming a ring.

The "heteroloweralkylidenyl" radical refers to an alkylidene hydrocarbon radical containing from 2 to 8 carbon atoms and one or more hereto atoms selected from oxygen, nitrogen and sulfur, thus forming a hetero ring.

"Aryl" refers to an aromatic ring preferably phenyl.

This invention further describes a new method for treatment of cardiovascular disorders by the administration of a therapeutically effective amount of an amidinourea compound of formula II

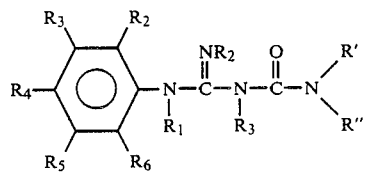

where:
$R_2$, $R_3$, $R_4$, $R_5$ and $R_6$ may be the same or different and are hydrogen, halo, haloloweralkyl, nitro, cyano, loweralkylsulfonyl, loweralkoxy or loweralkyl;
$R_1$, $R_2$ and $R_3$ are hydrogen or loweralkyl;
R' and R41 are hydrogen, loweralkyl, intermediate alkyl, loweralkenyl, cycloalkyl, cycloalkylloweralkyl, aralkyl, cycloalkenyl or aryl;
R' and R" together are loweralkylidenyl or heteroloweralkylidenyl;
provided $R_1$, $R_2$, $R_3$, R' and R" are not all hydrogen at the same time; and the non-toxic acid addition salts thereof.

The preferred compounds which are useful in the treatment of cardiovascular disorders are exemplified by those compounds of formula III

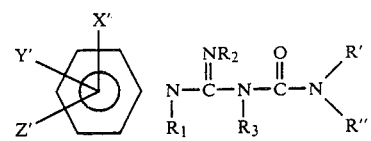

where:
X', Y' and Z' may be the same or different and are hydrogen, provided at least one of X', Y' and Z' is other than hydrogen, halo, haloloweralkyl or loweralkyl;
$R_1$, $R_2$ and $R_3$ are hydrogen or loweralkyl; and
R' and R" are hydrogen, loweralkyl or cycloalkyl;
provided $R_1$, $R_2$, $R_3$, R' and R" are not all hydrogen at the same time.

The more preferred compounds which are useful in the treatment of cardiovascular disorders are shown in formula III where:
X', Y' and Z' are hydrogen, provided at least one of X', Y' and Z' is other than hydrogen, halo, haloloweralkyl or loweralkyl;
$R_1$, $R_2$ and $R_3$ are hydrogen or methyl;
R' is hydrogen; and
R" is hydrogen, methyl, ethyl, propyl, i-propyl, butyl, t-butyl, cyclopropyl, cyclobutyl, cyclopentyl or cyclohexyl;
provided $R_1$, $R_2$, $R_3$, R' and R" are not all hydrogen at the same time.

The most preferred compounds are described by formula III where:
X' is hydrogen, chloro, bromo, fluoro, methyl or ethyl;
Y' is hydrogen, chloro, bromo, fluoro, methyl, ethyl or trifluoromethyl;
Z' is chloro, bromo, fluoro, methyl, ethyl or trifluoromethyl;
$R_1$, $R_2$ and $R_3$ are hydrogen or methyl;
R' is hydrogen; and
R" is hydrogen, methyl, ethyl, propyl, i-propyl, butyl or t-butyl;
provided $R_1$, $R_2$, $R_3$, R' and R" are not all hydrogen at the same time.

A special embodiment of this invention is described where X is hydrogen, Y is 2-chloro and Z is 6-chloro.

Another special embodiment is described where X and Y are hydrogen and Z is fluoro.

A further special embodiment is described where X is 2-methyl or 2-ethyl; Y is hydrogen; and Z is in the 6-position and is chloro, bromo, fluoro, methyl or ethyl.

Another special embodiment is described where X is in the 6-position and is chloro, bromo or fluoro; Y is in the 4-position and is methyl, ethyl, bromo or fluoro; and Z is in the 2-position and is chloro, bromo or fluoro.

A further embodiment is described where X is 2-methyl or 2-ethyl; Y is in the 4-position and is methyl, ethyl, chloro, bromo or fluoro; and Z is in the 6-position and is methyl, ethyl, chloro, bromo or fluoro.

It is well known in the pharmacological arts that non-toxic acid addition salts of pharmacologically active amine compounds do not differ in activities from their free base. The salts merely provide a convenient solubility factor.

The amines of this invention may be readily converted to their non-toxic acid addition salts by customary methods in the art. The non-toxic salts of this invention are those salts the acid component of which is pharmacologically acceptable in the intended dosages; such salts would include those prepared from inorganic acids, organic acids, higher fatty acids, high molecular weight acids, etc., and include such as:
hydrochloric acid,
hydrobromic acid,
sulfuric acid,
nitric acid,
phosphoric acid,
methanesulfonic acid,
benzenesulfonic acid,
acetic acid,
propionic acid,
malic acid,
succinic acid,
glycolic acid,
lactic acid,
salicylic acid,
benzoic acid,
nicotinic acid,
phthalic acid,
stearic acid,
oleic acid,
abietic acid, etc.

Representative compounds of this invention which are particularly useful are as follows:
1-(2,6-dichlorophenylamidino)-3-(t-butyl)urea
1-(p-chlorophenylamidino)-3-(t-butyl)urea
1-(2,4-dichlorophenylamidino)-3-(t-butyl)urea
1-(2,4,6-trichlorophenylamidino)-3-(t-butyl)urea
1-(p-bromophenylamidino)-3-(t-butyl)urea
1-(2,4-dibromophenylamidino)-3-(t-butyl)urea
1-(2-chloro-4-bromophenylamidino)-3-(t-butyl)urea
1-(2-fluoro-4-chlorophenylamidino)-3-(t-butyl)urea
1-(2-fluoro-6-chlorophenylamidino)-3-(t-butyl)urea
1-(2-chloro-4-fluorophenylamidino)-3-(t-butyl)urea
1-(p-fluorophenylamidino)-3-(t-butyl)urea
1-(2,4-difluorophenylamidino)-3-(t-butyl)urea
1-(2,6-difluorophenylamidino)-3-(t-butyl)urea
1-(p-trifluoromethylphenylamidino)-3-(t-butyl)urea
1-(p-trifluoromethoxyphenylamidino)-3-(t-butyl)urea
1-(p-methylsulfonylphenylamidino)-3-(t-butyl)urea
1-(p-nitrophenylamidino)-3-(t-butyl)urea
1-(2-chloro-4-nitrophenylamidino)-3-(t-butyl)urea
1-(2-bromo-4-nitrophenylamidino)-3-(t-butyl)urea
1-(2-fluoro-4-nitrophenylamidino)-3-(t-butyl)urea
1-(2-chloro-4-cyanophenylamidino)-3-(t-butyl)urea
1-(2-methyl-4-chlorophenylamidino)-3-(t-butyl)urea
1-(2-methyl-4-bromophenylamidino)-3-(t-butyl)urea
1-(2-methyl-4-fluorophenylamidino)-3-(t-butyl)urea
1-(2-chloro-4-methylphenylamidino)-3-(t-butyl)urea
1-(2-fluoro-4-methylphenylamidino)-3-(t-butyl)urea
1-(2-methyl-6-chlorophenylamidino)-3-(t-butyl)urea
1-(2-methyl-6-fluorophenylamidino)-3-(t-butyl)urea
1-(2,4-dimethylphenylamidino)-3-(t-butyl)urea
1-(2,6-dimethylphenylamidino)-3-(t-butyl)urea
1-(4-trifluoromethyl-2-chlorophenylamidino)-3-(t-butyl)urea
1-(4-trifluoromethyl-2-fluorophenylamidino)-3-(t-butyl)urea
1-(2,4-dichloro-6-methylphenylamidino)-3-(t-butyl)urea
1-(2,6-dichloro-4-methylphenylamidino)-3-(t-butyl)urea
1-(3,5-ditrifluoromethylphenylamidino)-3-(t-butyl)urea
1-(2-trifluoromethyl-4-nitrophenylamidino)-3-(t-butyl)urea
1-(2,6-dimethyl-4-chlorophenylamidino)-3-(t-butyl)urea
1-(2,6-dimethyl-4-fluorophenylamidino)-3-(t-butyl)urea
1-(2,6-dimethyl-4-nitrophenylamidino)-3-(t-butyl)urea
1-(2,6-dimethyl-4-trifluoromethylphenylamidino)-3-(t-butyl)urea
1-(2-ethyl-4-nitrophenylamidino)-3-(t-butyl)urea
1-(2,4-dichloro-6-fluorophenylamidino)-3-(t-butyl)urea
1-(2-chloro-4-methyl-6-fluorophenylamidino)-3-(t-butyl)urea
1-(2,4-dimethyl-6-chlorophenylamidino)-3-(t-butyl)urea
1-(2,4-dimethyl-6-fluorophenylamidino)-3-(t-butyl)urea
1-(2-chloro-4-fluoro-6-methylphenylamidino)-3-(t-butyl)urea
1-(2,6-dichloro-4-fluorophenylamidino)-3-(t-butyl)urea
1-(2-chloro-4-bromo-6-fluorophenylamidino)-3-(t-butyl)urea
1-(2,6-dichlorophenyl-N-methylamidino)urea
1-(2,6-dichlorophenyl-N-methylamidino)-3-(t-butyl)urea
1-(2,6-dichlorophenylamidino)-1-methylurea
1-(2,6-dichlorophenyl-N-methylamidino)-1-methylurea
1-(2,6-dichlorophenyl-N'-methylamidino)urea
1-(2,6-dichlorophenylamidino)-3,3-($\alpha,\alpha'$-dimethylpentamethylene)urea
1-(2,6-dichlorophenyl-N-methylamidino)-3,3-diethylurea The compounds of this invention exert activity on the cardiovascular system. They possess blood-pressure lowering effects and are useful as antihypertensive agents.

For these purposes, the amidinoureas of this invention can be normally administered orally or parenterally. Orally they may be administered as tablets, aqueous or oily suspensions, dispersible powders or granules, emulsions, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents, preserving agents and the like, in order to provide a pharmaceutically elegant and palatable preparation.

The dosage regimen in carrying out the methods of this invention is that which insures maximum therapeutic response until improvement is obtained and thereafter the minimum effective level which gives relief. Thus, in general, the dosages are those that are therapeutically effective in the alleviation of hypertensive disorders. In general, the daily dose can be between about 0.05 mg/kg/day and 70 mg/kg/day (preferably in the range of 1–25 mg/kg/day), bearing in mind, of course, that in selecting the appropriate dosage in any specific case, consideration must be given to the patient's weight, general health, age, and other factors which may influence response to the drug.

Various tests in animals have been carried out to show the ability of the compounds of this invention to exhibit reactions that can be correlated with activity in humans.

One such test is the ability of the compound to lower blood pressure in the spontaneous hypertensive rat (Ryo Tabei, et al., Clin. Pharm. & Therap. 11: 269–274, 1970). Blood pressure measurements are recorded by both the tail cuff method and by direct cannulation of a common carotid artery. Compounds that are effective antihypertensives in man have been shown to be active in lowering blood pressure in this animal model. In view of the results of this rest, the amidinoureas of this invention can be considered to be active antihypertensive agents.

The compounds of this invention may be prepared by the following general synthesis:

Condensation of cyanamide and a substituted aniline results in the corresponding substituted phenylguanidine.

The reaction is preferably carried out on the aniline salt either in a polar medium or neat and using increased temperatures. The salt used may be any acid addition amine salt but preferably the salt of a mineral acid. The polar medium may be aqueous, partially aqueous or a non-aqueous solution. It is convenient to choose a solvent that will reflux at the desired reaction temperature. The more preferred solvents are water or alcohol but other solvents may be used such as DMSO, diethyleneglycol, ethyleneglycol, tetrahydrofuran, dimethylformamide, etc. The most preferred solvent is a mildly acidic solvent which is non-nucleophilic such as phenol, cresol, xylenol, etc. The reaction should also be carried out at a temperature which is high enough so that condensation takes place readily, but not sufficient to decompose the guanidine formed. The reaction temperature can vary from room temperature to about 250° C. although it is preferable to run the reaction at temperatures from about 50° C. to 150° C. The guanidine salt which is formed can be converted to the free base with a metal hydroxide or alkoxide solution. The isolation of the desired guanidine can be carried out by any method known in the art.

When the substituted phenylguanidine is reacted with a substituted isocyanate of the formula R'NCO, then the product formed is a 1-substituted phenylamidino-3-R' urea. This reaction is preferably carried out in a non-polar medium using solvents such as benzene, toluene, xylene, etc. The reaction is also carried out as above at raised temperatures.

The following reaction equations illustrate this synthesis:

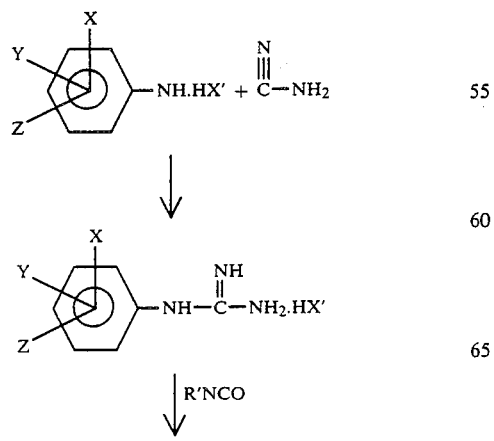

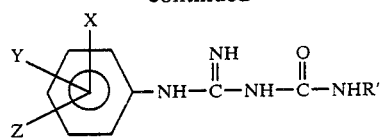

where:
HX' is a mineral acid and R' is other than hydrogen.

When $R_1$ substitution is desired, it is convenient to carry out the condensation using the appropriately N-substituted aniline. Thus, for example, N-methyl-2,6-dichloroaniline would result in the 1-(2,6-dichlorophenyl)-1-methylguanidine. This is then reacted as above with the isocyanate to form the amidinourea.

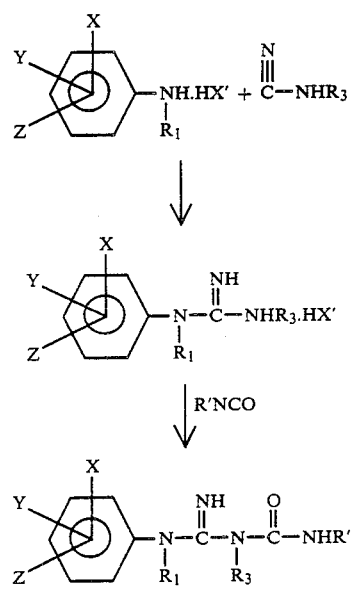

It is convenient to use t-butylisocyanate in the above reaction when $R_3$ is not desired. This may then be selectively hydrolyzed off.

When $R_3$ substitution is desired, it is convenient to carry out the condensation using the appropriately substituted cyanamide of the formula NHNHR$_3$. Thus, for example, methylcyanamide condensed with 2,6-dichloroaniline would result in the corresponding 1-(2,6-dichlorophenyl)-3-ethylguanidine. This is then reacted as above with the isocyanate to form the amidinoureas.

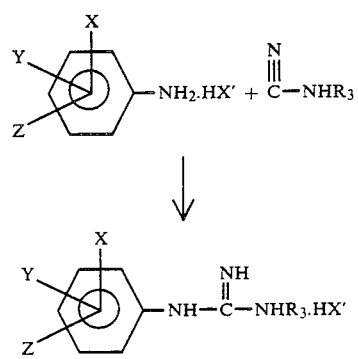

-continued

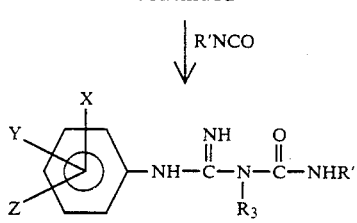

Condensation of an aniline with benzoylthiourea results in the 1-substitutedphenyl-3-benzoylthiourea. This may then be hydrolyzed to the 1-substitutedphenylthiourea and treated with iodomethane to obtain the 1-substitutedphenyl-2-methyl-pseudothiouronium iodide. When the latter is treated with an amine of the formula $NH_2R_1$, the resultant displacement yields a 1-substitutedphenyl-3-$R_1$ guanidine which may then be reacted as above to form the amidinourea.

$NH_4SCN + \phi COCL \longrightarrow$ 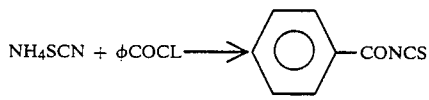

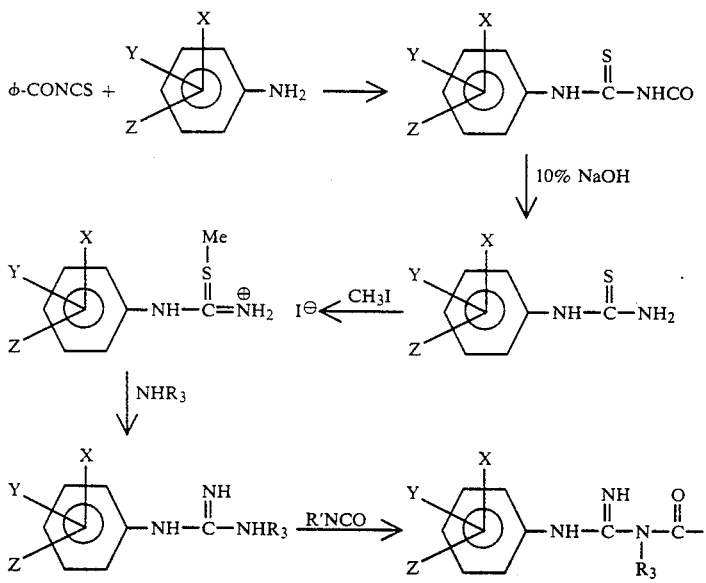

These compounds may also be prepared by condensing the desired aniline with a substituted isothiourea or with a thiocyanate of the formula $SCNR_3$. The latter reaction product is the thiourea which is then treated with iodomethane and reacted with an amine of the formula $NH_2R_2$ to obtain the desired guanidine. The above guanidine compounds are reacted with an isocyanate as above to obtain the amidinourea.

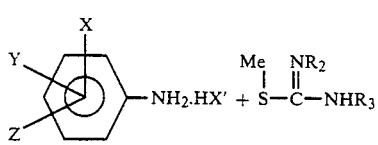

-continued

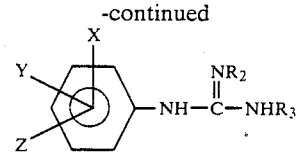

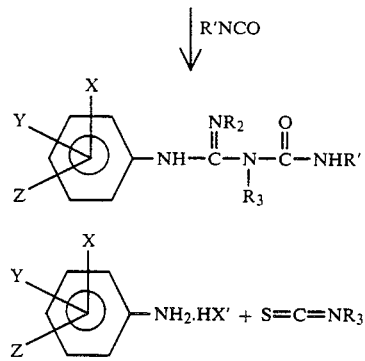

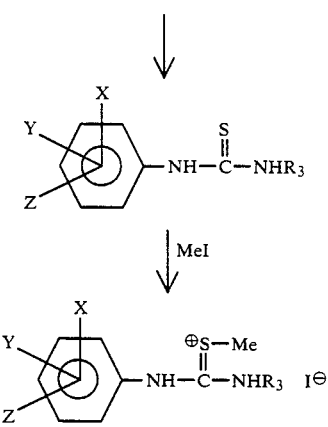

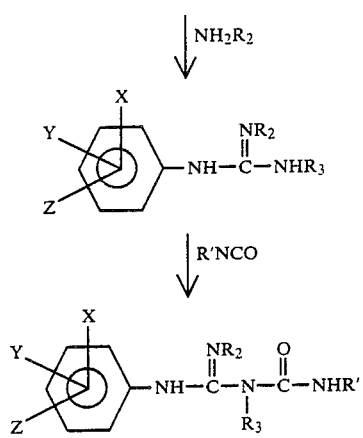

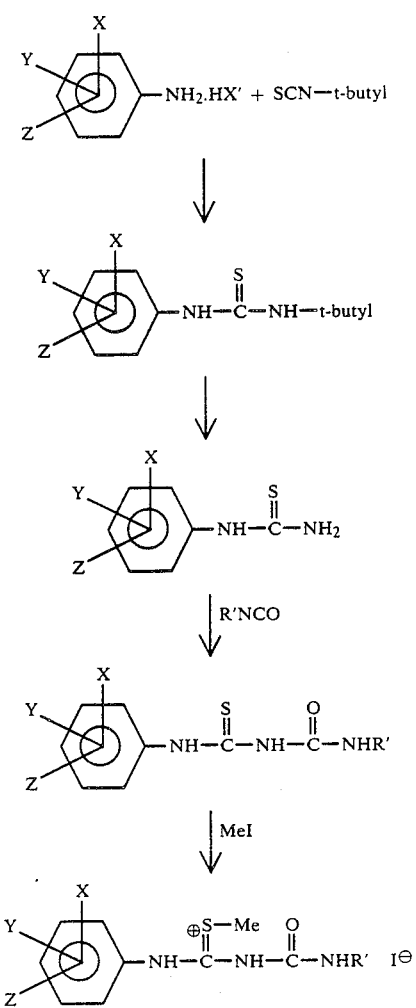

When $R_2$ substitution is desired the aniline is condensed with t-butyl thiocyanate of the formula SCN-t-butyl to form the thiourea. The t-butyl group is then hydrolyzed off with conc. HCl. The product is reacted with an isocyanate to obtain the carbamylthiourea, which is treated with iodomethane and reacted with an amine of the formula $NHR_2$ to obtain the desired amidinourea.

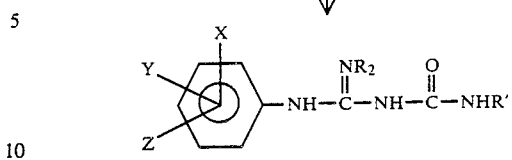

When R' and R'' substitution is desired the appropriate guanidine is reacted with the acid chloride of the amine of the formula

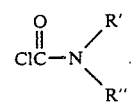

The latter is made by the reaction of the amine of the formula

with phosgene in an inert solvent. The reaction of the acid chloride and guanidine is carried out in a polar medium and inert conditions at moderate temperatures.

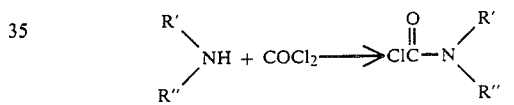

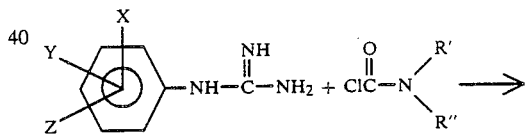

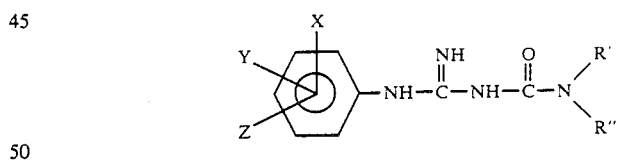

Appropriately desired end products having various X, Y and Z substituents may be prepared at various steps of synthesis using suitable reactions in order to convert one group to another.

The starting anilines are either known, may be prepared by known techniques or reference to the preparation is shown. Thus, chlorination or bromination of an acetanilide or aniline may be carried out in acetic acid, or in the presence of a small amount of iodine dissolved in an inert solvent such as carbon tetrachloride. A solution of chlorine or bromine is then added while the temperature is held near 0° C. iodination may also be carried out by known methods using iodine monochloride (ClI).

Alkylation may be carried out on an acetanilide using alkyl halide and aluminum chloride under Friedel-Crafts conditions to obtain desired alkyl substitution.

Nitration may be carried out using fuming nitric acid at about 0° C.

A nitro compound may be hydrogenated to the corresponding amine which may then be diazotized and heated in an alcohol medium to form the alkoxy compound.

An amino compound may also be diazotized to the diazonium fluoroborate which is then thermally decomposed to the fluoro compound. Diazotization followed by a Sandmeyer type reaction may yield the bromo, chloro or iodo compound.

Diazotization of an amino compound followed by addition of cuprous cyanide may result in the desired cyano compound.

When an amino compound is diazotized followed by reaction with potassium ethylxanthate and then hydrolyzed, the mercapto compound results. This in turn may be alkylated to the alkylthio group which is then oxidized to the corresponding alkylsulfonyl substituent.

A halo compound in which halo is chloro or bromo or iodo may be reacted with cuprous cyanide in guanidine at about 150° C. to produce a cyano compound.

A chloro, bromo or iodo compound may also be reacted with trifluoromethyliodide and copper powder at about 150° C. in dimethylformamide to obtain a trifluoromethyl compound [Tetrahedron Letters: 47, 4095 (1959)].

A halo compound may also be reacted with cuprous methanesulfinate in quinoline at about 150° C. to obtain a methylsulfonyl compound.

Of course the above reaction may also be carried out on acetophenone in order to direct substitution. Formation of an oxime followed by Beckmann Rearrangement results in the acetamide which is then deacylated to the aniline.

Reactions may also be carried out on the substituted anilines which would result in di- and tri-substituted anilines.

Reactions may also be carried out at other stages of synthesis depending on the substituents present and the substituents desired and various combinations of the foregoing reactions will be determined by one skilled in the art in order that the desired product results. Thus, a phenylguanidine or amidinourea may be halogenated or nitrated as above, etc.

The following are detailed examples which show the preparation of the compounds of this invention. They are to be construed as illustrations of said compounds and not as limitations thereof.

EXAMPLE 1

2,6-Dichlorophenylguanidine

To 51 g (0.315 mole) of 2,6-dichloroaniline is added 0.4 moles of ethereal HCl and 200 l of m-cresol. The mixture is then stirred and heated on a steam bath to drive off the ether and excess hydrogen chloride. To the resultant mixture is then added 13.3 g (0.315 mole) of cyanamide then heated for 2 hours on a steam bath. The reaction mixture is then cooled, added to 150 ml of conc. sodium hydroxide solution, cooled and extracted with 2 liters of ether. The ether layer is washed with 2×1 liter of water, dried over sodium sulfate, charcoaled and evaporated. The residue is triturated with hexane and the precipitate is filtered off and washed with ether and dried to obtain 2,6-dichlorophenylguanidine hydrochloride.

The free base is prepared by dissolving 2,6-dichlorophenylguanidine hydrochloride in 10% sodium hydroxide solution and extracting with ether. The ether is dried and evaporated to dryness to obtain 2,6-dichlorophenylguanidine.

When the above procedures are followed using the amines of Table I, below, then the corresponding product of Table II, below, is prepared.

TABLE I o-chloroaniline
m-chloroaniline
p-chloroaniline
2,3-dichloroaniline
2,4-dichloroaniline
2,5-dichloroaniline
3,4-dichloroaniline
3,5-dichloroaniline
2,3,4-trichloroaniline
2,3,5-trichloroaniline
2,3,6-trichloroaniline
2,4,5-trichloroaniline
2,4,6-trichloroaniline
3,4,5-trichloroaniline
o-bromoaniline
m-bromoaniline
p-bromoaniline
2,3-dibromoaniline
2,4-dibromoaniline
2,5-dibromoaniline
2,6-dibromoaniline
3,4-dibromoaniline
3,5-dibromoaniline
2-chloro-3-bromoaniline
2-chloro-4-bromoaniline
2-chloro-5-bromoaniline
2-chloro-6-bromoaniline
3-chloro-2-bromoaniline
3-chloro-4-bromoaniline
3-chloro-5-bromoaniline
3-chloro-6-bromoaniline
4-chloro-2-bromoaniline
4-chloro-3-bromoaniline
2-fluoro-4-chloroaniline
2-fluoro-6-chloroaniline
2-chloro-4-bromoaniline
2-fluoro-6-bromoaniline
2-bromo-4-fluoroaniline
2-iodo-4-chloroaniline
2-iodo-6-chloroaniline
2-chloro-4-iodoaniline
2-iodo-4-bromoaniline
o-fluoroaniline
m-fluoroaniline
p-fluoroaniline
p-iodoaniline
2,4-difluoroaniline
2,5-difluoroaniline
2,6-difluoroaniline
2,4-diiodoaniline
2-iodo-6-bromoaniline
2-bromo-4-iodoaniline
2-fluoro-4-iodoaniline
2-iodo-4-fluoroaniline
o-trifluoromethylaniline
m-trifluoromethylaniline
p-trifluoromethylaniline
p-trifluoromethoxyaniline
p-methylsulfonylaniline
o-nitroaniline
m-nitroaniline
p-nitroaniline
2-chloro-4-nitroaniline
2-bromo-4-nitroaniline
2-iodo-4-nitroaniline
2-fluoro-4-nitroaniline
2-nitro-4-chloroaniline
2-nitro-4-bromoaniline
2-nitro-4-fluoroaniline
2-nitro-4-trifluoromethylaniline
2-nitro-4-methoxyaniline
2-cyano-4-chloroaniline
2-chloro-4-cyanoaniline
2-methyl-4-chloroaniline

TABLE I-continued 2-methyl-4-bromoaniline
2-methyl-4-fluoroaniline
2-chloro-4-methylaniline
2-bromo-4-methylaniline
2-fluoro-4-methylaniline
2-cyano-4-methylaniline
2-trifluoromethyl-4-methylaniline
2-methyl-4-nitroaniline
2-methyl-4-cyanoaniline
2-methyl-4-trifluoromethylaniline
2-chloro-6-nitroaniline
2-bromo-6-nitroaniline
2-iodo-6-nitroaniline
2-fluoro-6-nitroaniline
2-nitro-6-trifluoromethylaniline
2-nitro-6-methoxyaniline
2-cyano-6-chloroaniline
2-methyl-6-chloroaniline
2-methyl-6-bromoaniline
2-methyl-6-fluoroaniline
2-methyl-6-nitroaniline
2-methyl-6-trifluoromethylaniline
2-methyl-6-cyanoaniline
2-methyl-6-methylsulfonylaniline
2,4-dimethylaniline
2,6-dimethylaniline
2-trifluoromethyl-6-chloroaniline
2-trifluoromethyl-6-bromoaniline
2-trifluoromethyl-6-flouroaniline
2-trifluoromethyl-6-nitroaniline
2-trifluoromethyl-4-chloroaniline
2-trifluoromethyl-4-bromoaniline
2-trifluoromethyl-4-fluoroaniline
4-trifluoromethyl-2-chloroaniline
4-trifluoromethyl-2-bromoaniline
4-trifluoromethyl-2-fluoroaniline
2,4-dichloro-6-methylaniline
2,6-dichloro-4-methylaniline
3,5-ditrifluoromethylaniline
2-methoxy-4-nitroaniline
2-trifluoromethyl-4-nitroaniline
2,4-dichloro-6-methoxyaniline
2,6-dimethyl-4-chloroaniline
2,6-dimethyl-4-fluoroaniline
2,6-dimethyl-4-bromoaniline
2,6-dimethyl-4-nitroaniline
2,6-dimethyl-4-trifluoromethylaniline
2-ethyl-4-nitroaniline
2-ethyl-4-chloroaniline
2-ethyl-4-bromoaniline
2-ethyl-4-fluoroaniline
2-ethyl-4-trifluoromethylaniline
2-ethyl-4-cyanoaniline
2-ethyl-4-methylsulfonylaniline
2,4-dichloro-6-bromoaniline
2,6-dichloro-4-bromoaniline
2,4-dibromo-6-chloroaniline
2,6-dibromo-4-chloroaniline
2,4-dichloro-6-fluoroaniline
2-chloro-4-methyl-6-fluoroaniline
2,4-dimethyl-6-chloroaniline
2,4-dimethyl-6-fluoroaniline
2-chloro-4-fluoro-6-methylaniline
2,6-dichloro-4-fluoroaniline
2,5-dichloro-4-fluoroaniline
2,4-dichloro-6-iodoaniline
2,6-dichloro-4-iodoaniline
2,4-dibromo-6-iodoaniline
2,4-bromo-6-fluoroaniline
2,6-dibromo-4-fluoroaniline
2-chloro-4-bromo-6-fluoroaniline
2-bromo-4-fluoro-6-chloroaniline
2-bromo-4-chloro-6-fluoroaniline
2-chloro-4-iodo-6-bromoaniline
2,4,6-tribromoaniline
2,4,6-trifluoroaniline

TABLE II o-chlorophenylguanidine

TABLE II-continued m-chlorophenylguanidine
p-chlorophenylguanidine
2,3-dichlorophenylguanidine
2,4-dichlorophenylguanidine
2,5-dichlorophenylguanidine
3,4-dichlorophenylguanidine
3,5-dichlorophenylguanidine
2,3,4-trichlorophenylguanidine
2,3,5-trichlorophenylguanidine
2,3,6-trichlorophenylguanidine
2,4,5-trichlorophenylguanidine
2,4,6-trichlorophenylguanidine
3,4,5-trichlorophenylguanidine
o-bromophenylguanidine
m-bromophenylguanidine
p-bromophenylguanidine
2,3-dibromophenylguanidine
2,4-dibromophenylguanidine
2,5-dibromophenylguanidine
2,6-dibromphenylguanidine
3,4-dibromophenylguanidine
3,5-dibromophenylguanidine
2-chloro-3-bromophenylguanidine
2-chloro-4-bromophenylguanidine
2-chloro-5-bromophenylguanidine
2-chloro-6-bromophenylguanidine
3-chloro-2-bromophenylguanidine
3-chloro-4-bromophenylguanidine
3-chloro-5-bromophenylguanidine
3-chloro-6-bromophenylguanidine
4-chloro-2-bromophenylguanidine
4-chloro-3-bromophenylguanidine
2-fluoro-4-chlorophenylguanidine
2-fluoro-6-chlorophenylguanidine
2-chloro-4-fluorophenylguanidine
2-fluoro-6-bromophenylguanidine
2-bromo-4-fluorophenylguanidine
2-iodo-4-chlorophenylguanidine
2-iodo-6-chlorophenylguanidine
2-chloro-4-iodophenylguanidine
2-iodo-4-bromophenylguanidine
o-fluorophenylguanuidine
m-fluorophenylguanidine
p-fluorophenylguanidine
p-iodophenylguanidine
2,4-difluorophenylguanidine
2,5-difluorophenylguanidine
2,6-difluorophenylguanidine
2,4-diiodophenylguanidine
2-iodo-6-bromophenylguanidine
2-bromo-4-iodophenylguanidine
2-fluoro-4-iodophenylguanidine
2-iodo-4-fluorophenylguanidine
o-trifluoromethylphenylguanidine
m-trifluoromethylphenylguanidine
p-trifluoromethylphenylguanidine
p-trifluoromethoxyphenylguanidine
p-methylsulfonylphenylguanidine
o-nitrophenylguanidine
m-nitrophenylguanidine
p-nitrophenylguanidine
2-chloro-4-nitrophenylguanidine
2-bromo-4-nitrophenylguanidine
2-iodo-4-nitrophenylguanidine
2-fluoro-4-nitrophenylguanidine
2-nitro-4-chlorophenylguanidine
2-nitro-4-bromophenylguanidine
2-nitro-4-fluorophenylguanidine
2-nitro-4-trifluoromethylphenylguanidine
2-nitro-4-methoxyphenylguanidine
2-cyano-4-chlorophenylguanidine
2-chloro-4-cyanophenylguanidine
2-methyl-4-chlorophenylguanidine
2-methyl-4-bromophenylguanidine
2-methyl-4-fluorophenylguanidine
2-chloro-4-methylphenylguanidine
2-bromo-4-methylphenylguanidine
2-fluoro-4-methylphenylguanidine
2-cyano-4-methylphenylguanidine
2-trifluoromethyl-4-methylphenylguanidine
2-methyl-4-nitrophenylguanidine
2-methyl-4-cyanophenylguanidine

TABLE II-continued 2-methyl-4-trifluoromethylphenylguanidine
2-chloro-6-nitrophenylguanidine
2-bromo-6-nitrophenylguanidine
2-iodo-6-nitrophenylguanidine
2-fluoro-6-nitrophenylguanidine
2-nitro-6-trifluoromethylphenylguanidine
2-nitro-6-methoxyphenylguanidine
2-cyano-6-chlorophenylguanidine
2-methyl-6-chlorophenylguanidine
2-methyl-6-bromophenylguanidine
2-methyl-6-fluorophenylguanidine
2-methyl-6-nitrophenylguanidine
2-methyl-6-trifluoromethylphenylguanidine
2-methyl-6-cyanopnenylguanidine
2-methyl-6-methylsulfonylphenylguanidine
2,4-dimethylphenylguanidine
2,6-dimethylphenylguanidine
2-trifluoromethyl-6-chlorophenylguanidine
2-trifluoromethyl-6-bromophenylguanidine
2-trifluoromethyl-6-fluorophenylguanidine
2-trifluoromethyl-6-nitrophenylguanidine
2-trifluoromethyl-4-chlorophenylguanidine
2-trifluoromethyl-4-bromophenylguanidine
2-tifluoromethyl-4-fluorophenylguanidine
4-tifluoromethyl-2-chlorophenylguanidine
4-trifluoromethyl-2-bromophenylguanidine
4-trifluoromethyl-2-bromophenylguanidine
2,4-dichloro-6-methylphenylguanidine
2,6-dichloro-4-methylphenylguanidine
3,5-ditrifluoromethylphenylguanidine
2-methoxy-4-nitrophenylguanidine
2-trifluoromethyl-4-nitrophenylguanidine
2,4-dichloro-6-methoxyphenylguanidine
2,6-dimethyl-4-chlorophenylguanidine
2,6-dimethyl-4-fluorophenylguanidine
2,6-dimethyl-4-bromophenylguanidine
2,6-dimethyl-4-nitrophenylguanidine
2,6-dimethyl-4-trifluoromethylphenyl-guanidine
2-ethyl-4-nitrophenylguanidine
2-ethyl-4-chlorophenylguanidine
2-ethyl-4-bromophenylguanidine
2-ethyl-4-fluorophenylguanidine
2-ethyl-4-trifluoromethylphenylguanidine
2-ethyl-4-cyanophenylguanidine
2-ethyl-4-methylsulfonylphenylguanidine
2,4-dichloro-6-bromophenylguanidine
2,6-dichloro-4-bromophenylguanidine .
2,4-dibromo-6-chlorophenylguanidine
2,6-dibromo-4-chlorophenylguanidine
2,4-dichloro-6-fluorophenylguanidine
2-chloro-4-methyl-6-fluorophenylguanidine
2,4-dimethyl-6-chlorophenylguanidine
2,4-dimethyl-6-fluorophenylguanidine
2-chloro-4-flouro-6-methylphenylguanidine
2,6-dichloro-4-fluorophenylguanidine
2,5-dichloro-4-fluorophenylguanidine
2,4-dichloro-6-iodophenylguanidine
2,6-dichloro-4-iodophenylguanidine
2,4-dibromo-6-iodophenylguanidine
2,4-dibromo-6-fluorophenylguanidine
2,6-dibromo-4-fluorophenylguanidine
2-chloro-4-bromo-6-fluorophenylguanidine
2-bromo-4-fluoro-6-chlorophenylguanidine
2-bromo-4-chloro-6-fluorphenylguanidine
2-chloro-4-iodo-6-bromophenylguanidine
2,4,6-tribromophenylguanidine
2,4,6-trifluorophenylguanidine

EXAMPLE 2

1-(2,6-dichlorophenyl)-1-methylguanidine

To 55.4 (0.315 mole) of N-methyl-2,6-dichloroaniline is added 0.4 moles of ethereal HCl and 200 ml of m-cresol. The mixture is then stirred and heated on a steam bath to drive off the ether and excess hydrogen chloride. To the resultant mixture is then added 13.3 g (0.315 mole) of cyanmide then heated for 2 hours on a steam bath. The reaction mixture is then cooled, added to 150 ml of conc. sodium hydroxide solution, cooled and extracted with 2 liters of ether. The ether layer is washed with 2×1 liter of water, dried over sodium sulfate, charcoaled and evaporated. The residue is triturated with hexane and the precipitate is filtered off and washed with ether and dried to obtain 1-(2,6-dichlorophenyl)-1-methylguanidine hydrochloride.

The free base is prepared by dissolving 1-(2,6-dichlorophenyl)-1-methylguanidine hydrochloride in 10% sodium hydroxide solution and extracting with ether. The ether is dried and evaporated to dryness to obtain 1-(2,6-dichlorophenyl)-1-methylguanidine.

When the N-methylaniline in the above procedures is replaced by the N-loweralkylanilines of this invention then the corresponding product is obtained.

When the above procedures are followed using the representative amines of Table I, below, then the corresponding product of Table II, below, is prepared.

TABLE I

N—methyl-p-chloroaniline
N—methyl-2,3-dichloroaniline
N—methyl-2,4-dichloroaniline
N—methyl-2,5-dichloroaniline
N—methyl-3,4-dichloroaniline
N—methyl-3,5-dichloroaniline
N—methyl-2,3,4-trichloroaniline
N—methyl-2,3,5-trichloroaniline
N—methyl-2,3,6-trichloroaniline
N—methyl-2,4,5-trichloroaniline
N—methyl-2,4,6-trichloroaniline
N—methyl-3,4,5-trichloroaniline
N—methyl-p-bromoaniline
N—methyl-2,4-dibromoaniline
N—methyl-2-chloro-4-bromaoniline
N—methyl-2-chloro-6-bromoaniline
N—methyl-3-chloro-4-bromoaniline
N—methyl-3-chloro-5-bromoaniline
N—methyl-4-chloro-2-bromoaniline
N—methyl-2-fluoro-4-chloroaniline
N—methyl-2-fluoro-6-chloroaniline
N—methyl-2-chloro-4-fluoroaniline
N—methyl-2-fluoro-6-bromoaniline
N—methyl-2-bromo-4-fluoroaniline
N—methyl-2-iodo-4-chloroaniline
N—methyl-2-iodo-6-chloroaniline
N—methyl-2-chloro-4-iodoaniline
N—methyl-2-iodo-4-bromoaniline
N—methyl-o-fluoroaniline
N—methyl-m-fluoroaniline
N—methyl-p-fluoroaniline
N—methyl-p-iodoaniline
N—methyl-2,4-difluoroaniline
N—methyl-2,6-difluoroaniline
N—methyl-2-fluoro-4-iodoaniline
N—methyl-o-trifluoromethylaniline
N—methyl-m-trifluoromethylaniline
N—methyl-p-trifluoromethylaniline
N—methyl-p-tifluoromethoxyaniline
N—methyl-p-methylsulfonylaniline
N—methyl-p-nitroaniline
N—methyl-2-chloro-4-nitroaniline
N—methyl-2-bromo-4-nitroaniline
N—methyl-2-fluoro-4-nitroaniline
N—methyl-2-nitro-4-chloroaniline
N—methyl-2-nitro-4-bromoaniline
N—methyl-2-nitro-4-fluoroaniline
N—methyl-2-nitro-4-trifluoromethyl-aniline
N—methyl-2-nitro-4-methoxyaniline
N—methyl-2-methyl-4-chloroaniline
N—methyl-2-methyl-4-bromoaniline
N—methyl-2-methyl-4-fluoroaniline
N—methyl-2-chloro-4-methylaniline
N—methyl-2-bromo-4-methylaniline
N—methyl-2-fluoro-4-methylaniline
N—methyl-2-cyano-4-methylaniline
N—methyl-2-trifluoromethyl-4-methylaniline
N—methyl-2-methyl-4-nitroaniline

TABLE I-continued

N—methyl-2-methyl-4-cyanoaniline
N—methyl-2-methyl-4-trifluoromethylaniline
N—methyl-2-chloro-6-nitroaniline
N—methyl-2-bromo-6-nitroaniline
N—methyl-2-iodo-6-nitroaniline
N—methyl-2-fluoro-6-nitroaniline
N-methyl-2-nitro-6-trifluoromethylaniline
N—methyl-2-nitro-6-methoxyaniline
N—methyl-2-methyl-6-chloroaniline
N—methyl-2-methyl-6-bromoaniline
N—methyl-2-methyl-6-fluoroaniline
N—methyl-2-methyl-6-nitroaniline
N—methyl-2-methyl-6-trifluoromethylaniline
N—methyl-2-methyl-6-cyanoaniline
N—methyl-2,4-dimethylaniline
N—methyl-2,6-dimethylaniline
N—methyl-2-trifluoromethyl-6-chloroaniline
—methyl-2-trifluoyomethyl-6-bromoaniline
N—methyl-2-trifluoromethyl-6-fluoroaniline
N—methyl-2-trifluoromethyl-4-chloroaniline
N—methyl-2-trifluoromethyl-4-bromoaniline
N—methyl-2-trifluoromethyl-4-fluoroaniline
N—methyl-4-trifluoromethyl-2-chloroaniline
N—methyl-4-trifluoromethyl-2-bromoaniline
N—methyl-4-trifluoromethyl-2-fluoroaniline
N—methyl-2,4-dichloro-6-methylaniline
N—methyl-2,6-dichloro-4-methylaniline
dn—methyl-3,5-ditrifluoromethylaniline
N—methyl-2-trifluoromethyl-4-nitroaniline
N—methyl-2,6-dimethyl-4-chloroaniline
N—methyl-2,6-dimethyl-4-fluoroaniline
N—methyl-2,6-dimethyl-4-bromoaniline
N—methyl-2,6-dimethyl-4-nitroaniline
N—methyl-2,6-dimethyl-4-trifluoromethylaniline
N—methyl-2-ethyl-4-nitroaniline
N—methyl-2-ethyl-4-chloroaniline
N—methyl-2-ethyl-4-bromoaniline
N—methyl-2-ethyl-4-fluoroaniline
N—methyl-2-ethyl-4-trifluoromethylaniline
N—methyl-2-ethyl-4-cyanoaniline
N—methyl-2-ethyl-4-methylsulfonylaniline
N—methyl-2,4-dichloro-6-bromoaniline
N—methyl-2,6-dichloro-4-bromoaniline
N—methyl-2,4-dibromo-6-chloroaniline
N—methyl-2,6-dibromo-4-chloroaniline
N—methyl-2,4-dichloro-6-fluoroaniline
N—methyl-2,6-dichloro-4-fluoroaniline
N—methyl-2,5-dichloro-4-fluoroaniline
N—methyl-2,4-dichloro-6-iodoaniline
N—methyl-2,6-dichloro-4-iodoaniline

TABLE I-continued

N—methyl-2,4-dibromo-6-iodoaniline
N—methyl-2,4-dibromo-6-fluoroaniline
N—methyl-2,6-dibromo-4-fluoroaniline
N—methyl-2-chloro-4-bromo-6-fluoroaniline
N—methyl-2-bromo-4-fluoro-6-chloroaniline
N—methyl-2-bromo-4-chloro-6-fluoroaniline
N—methyl-2-bromo-4-fluoro-6-chloroaniline
N—methyl-2-bromo-4-chloro-6-fluoroaniline
N—methyl-2-chloro-4-iodo-6-bromoaniline
N—methyl-2,4,6-tribromoaniline
N—methyl-2,4,6-trifluoraniline
N—ethyl-2,6-dichloroaniline
N—ethyl-2,4-dichloroaniline
N—ethyl-p-fluoroaniline
N—propyl-p-fluoroaniline
N—i-propyl-p-fluoroaniline
N—butyl-p-fluoroaniline

TABLE II 1-(p-chlorophenyl)-1-methylguanidine
1-(2,3-dichlorophenyl)-1-methylguanidine
1-(2,4-dichlorophenyl)-1-methylguanidine
1-(2,5-dichlorophenyl)-1-methylguanidine
1-(3,4-dichlorophenyl)-1-methylguanidine
1-(3,5-dichlorophenyl)-1-methylguanidine
1-(2,3,4-trichlorophenyl)-1-methylguanidine
1-(2,3,5-trichlorophenyl)-1-methylguanidine
1-(2,3,6-trichlorophenyl)-1-methylguanidine
1-(2,4,5-trichlorophenyl)-1-methylguanidine
1-(2,4,6-trichlorophenyl)-1-methylguanidine
1-(3,4,5-trichlorophenyl)-1-methylguanidine
1(p-bromophenyl)-1-methylguanidine
1-(2,4-dibromophenyl)-1-methylguanidine
1-(2-chloro-4-bromophenyl)-1-methylguanidine
1-(2-chloro-6-bromophenyl)-1-methylguanidine
1-(3-chloro-4-bromophenyl)-1-methylguanidine
1-(3-chloro-5-bromophenyl)-1-methylguanidine
1-(4-chloro-2-bromophenyl)-1-methylguanidine
1-(2-fluoro-4-chlorophenyl)-1-methylguanidine
1-(2-fluoro-6-chlorophenyl)-1-methylguanidine
1-(2-chloro-4-fluorophenyl)-1-methylguanidine
1-(2-fluoro-6-bromophenyl)-1-methylguanidine
1-(2-bromo-4-fluorophenyl)-1-methylguanidine
1-(2-iodo-4-chlorophenyl)-1-methylguanidine
1-(2-iodo-6-chlorophenyl)-1-methylguanidine
1-(2-chloro-4-iodophenyl)-1-methylguanidine
1-(2-iodo-4-bromophenyl)-1-methylguanidine
1-(o-fluorophenyl)-1-methylguanidine
1-(m-fluorophenyl)-1-methylguanidine
1-(p-fluorophenyl)-1-methylguanidine
1-(p-iodophenyl)-1-methylguanidine
1-(2,4-difluorophenyl)-1-methylguanidine
1-(2,6-difluorophenyl)-1-methylguanidine
1-(2-fluoro-4-iodophenyl)-1-methylguanidine
1-(o-trifluoromethylphenyl)-1-methylguanidine
1-(m-trifluoromethylphenyl)-1-methylguanidine
1-(p-trifluoromethylphenyl)-1-methylguanidine
1-(p-trifluoromethoxyphenyl)-1-methylguanidine
1-(p-methylsulfonylphenyl)-1-methylguanidine
1-(p-nitrophenyl)-1-methylguanidine
1-(2-chloro-4-nitrophenyl)1-methylguanidine
1-(2-bromo-4-nitrophenyl)-1-methylguanidine
1-(2-fluoro-4-nitrophenyl)-1-methylguanidine
1-(2-nitro-4-chlorophenyl)-1-methylguanidine
1-(2-nitro-4-bromophenyl)-1-methylguanidine
1-(2-nitro-4-fluorophenyl)-1-methylguanidine
1-(2-nitro-4-trifluoromethylphenyl)-1-

TABLE II-continued methylguanidine
1-(2-nitro-4-methoxyphenyl)-1-methylguanidine
1-(2-methyl-4-chlorophenyl)-1-methylguanidine
1-(2-methyl-4-bromophenyl)-1-methylguanidine
1-(2-methyl-4-fluorophenyl)-1-methyl-
guanidine
1-(2-chloro-4-methylphenyl)-1-methyl-
guanidine
1-(2-bromo-4-methylphenyl)-1-methyl-
guanidine
1-(2-fluoro-4-methylphenyl)-1-methyl-
guanidine
1-(2-cyano-4-methylphenyl)-1-methyl-
guanidine
1-(2-trifluoromethyl-4-methylphenyl)-1-
methylguanidine
1-(methyl-4-nitrophenyl)-1-methylguanidine
1-(2-methyl-4-cyanophenyl)-1-methylguanidine
1-(2-methyl-4-trifluoromethylphenyl)-1-
methylguanidine
1-(chloro-6-nitrophenyl)-1-methylguanidine
1-(2-bromo-6-nitrophenyl)-1-methylguanidine
1-(2-iodo-6-nitrophenyl)-1-methylguanidine
1-(2-fluoro-6-nitrophenyl)-1-methylguanidine
1-(2-nitro-6-trifluoromethylphenyl)-1-
methylguanidine
1-(2-nitro-6-methoxyphenyl)-1-methyl-
guanidine
1-(2-methyl-6-chlorophenyl)-1-methyl-
guanidine
1-(2-methyl-6-bromophenyl)-1-methylguanidine
1-(2-methyl-6-fluorophenyl)-1-methyl
guanidine
1-(2-methyl-6-nitrophenyl)-1-methylguanidine
1-(2-methyl-6-trifluoromethylphenyl)-1-
methylguanidine
1-(2-methyl-6-cyanophenyl)-1-methylguanidine
1-(2,4-dimethylphenyl)-1-methylguanidine
1-(2,6-dimethylphenyl)-1-methylguanidine
1-(2-trifluoromethyl-6-chlorophenyl)-1-
methylguanidine
1-(2-trifluoromethyl-6-bromophenyl)-1-
methylguanidine
1-(2-trifluoromethyl-6-fluorophenyl)-1-
methylguanidine
1-(2-trifluoromethyl-4-chlorophenyl)-1-
methylguanidine
1-(2-trifluoromethyl-4-bromophenyl)-1-
methylguanidine
1-(2-trifluoromethyl-4-fluorophenyl)-1-
methylguanidine
1-(4-trifluoromethyl-2-chlorophenyl)-1-
methylguanidine
1-(4-trifluoromethyl-2-bromophenyl)-1-
methylguanidine
1-(4-trifluoromethyl-2-fluorophenyl)-1-
methylguanidine
1-(2,4-dichloro-6-methylphenyl)-1-
methylguanidine
1-(2,6-dichloro-4-methylphenyl)-1-
methylguanidine
1-(3,5-ditrifluoromethylphenyl)-1-
methylguanidine
1-(2-trifluoromethyl-4-nitrophenyl)-1-
methylguanidine
1-(2,6-dimethyl-4-chlorophenyl)-1-
methylguanidine
1-(2,6-dimethyl-4-fluorophenyl)-1-
methylguanidine
1-(2,6-dimethyl-4-bromophenyl)-1-
methylguanidine
1-(2,6-dimethyl-4-nitrophenyl)-1-
methylguanidine
1-(2,6-dimethyl-4-trifluoromethylphenyl)-1-
methylguanidine
1-(2-ethyl-4-nitrophenyl)-1-methylguanidine
1-(2-ethyl-4-chlorophenyl)-1-methylguanidine
1-(2-ethyl-4-bromophenyl)-1-methylguanidine
1-(2-ethyl-4-fluorophenyl)-1-methylguanidine
1-(2-ethyl-4-trifluoromethylphenyl)-1-
methylguanidine
1-(2-ethyl-4-cyanophenyl)-1-methylguanidine

TABLE II-continued 1-(2-ethyl-4-methylsulfonylphenyl)-1-
methylguanidine
1-(2,4-dichloro-6-bromophenyl)-1-
methylguanidine
1-(2,6-dichloro-4-bromophenyl)-1-
methylguanidine
1-(2,4-dibromo-6-chlorophenyl)-1-
methylguanidine
1-(2,6-dibromo-4-chlorophenyl)-1-
methylguanidine
1-(2,4-dichloro-6-fluorophenyl)-1-
methylguanidine
1-(2,6-dichloro-4-fluorophenyl)-1-
methylguanidine
1-(2,5-dichloro-4-fluorophenyl)-1-
methylguanidine
1-(2,4-dichloro-6-iodophenyl)-1-
methylguanidine
1-(2,6-dichloro-4-iodophenyl1-(2,6-dibromo-4-fluoro-
phenyl)-1-
methylguanidine
1-(2-chloro-4-bromo-6-fluorophenyl)-1-
methylguanidine
1-(2-bromo-4-fluoro-6-chlorophenyl)-1-
methylguanidine
1-(2-bromo-4-chloro-6-fluorophenyl)-1-
methylguanidine
1-(2-bromo-4-fluoro-6-chlorophenyl)-1-
methylguanidine
1-(2-bromo-4-chloro-6-fluorophenyl)-1-
methylguanidine
1-(2-chloro-4-iodo-6-bromophenyl)-1-
methylguanidine
1-(2,4,6-tribromophenyl)-1-methylguanidine
1-(2,4,6-trifluorophenyl)-1-methylguanidine
1-(2,6-dichlorophenyl)-1-ethylguanidine
1-(2,4-dichlorophenyl)-1-ethylguanidine
1-(p-fluorophenyl)-1-ethylguanidine
1-(p-fluorphenyl)-1-propylguanidine
1-(p-fluorophenyl)-1-i-propylguanidine
1-(p-fluorophenyl)-1-butylguanidine

EXAMPLE 3

1-(2,6-dichlorophenyl)-3-methylguanidine

To 51 g (0.315 mole) of 2,6-dichloroaniline is added 0.4 moles of ethereal HCl and 200 ml of m-cresol. The mixture is then sitrred and heated on a steam bath to drive off the ether and excess hydrogen chloride. To the resultant mixture is then added 17.7 g (0.315 mole) of methyl cyanamide then heated for 2 hours on a steam bath. The reaction mixture is then cooled, added to 150 ml of conc. sodium hydroxide solution, cooled and extracted with 2 liters of ether. The ether layer is washed with 2×1 liter of water, dried over sodium sulfate, charcoaled and evaporated. The residue is triturated with hexane and the precipitate is filtered off and washed with ether and dried to obtain 1-(2,6-dichlorophenyl)-3-methylguanidine hydrochloride.

The free base is prepared by dissolving 1-(2,6-dichlorophenyl)-3-methylguanidine hydrochloride to 10% sodium hydroxide solution and extracting with ether. The ether is dried and evaporated to dryness to obtain 1-(2,6-dichlorophenyl)-3-methylguanidine.

When the above procedures are followed using the cyanamides of Table I below, then the corresponding products are prepared.

TABLE I ethylcyanamide
propylcyanamide
i-propylcyanamide
butylcyanamide pentylcyanamide
hexylcyanamide
heptylcyanamide
octylcyanamide
vinylcyanamide
propargylcyanamide
methallylcyanamide
2,4-pentadienylcyanamide
2-pentenylcyanamide
cyclopropylcyanamide
cyclobutylcyanamide
cyclopentylcyanamide
cyclohexylcyanamide
phenylcyanamide
benzylcyanamide
phenethylcyanamide
cyclohex-2-enylcyanamide
cyclopropylmethylcyanamide
cyclobutylmethylcyanamide
cyclopropylethylcyanamide When the anilines of Examples 1 and 2 are condensed with the above cyanamides using the above procedures, then the corresponding products are obtained.

EXAMPLE 4

1-(p-flurophenyl)-3-methylthiourea

To a mixture of 55.5 g (0.5 mole) of p-fluoroaniline and 100 ml of xylene is added 36.5 g (0.5 mole) of methylisothiocyanate and the mixture is refluxed for 2 hours. The reaction product is cooled, titurated with haptane and filtered. Recrystallization from 1:1 isopropanol/water results in 1-(p-fluorophenyl)-3-methylthiourea.

When the above procedure is followed using 2,6-dichloroaniline then the product prepared is 1-(2,6-dichlorophenyl)-3-methylthiourea.

When the above procedure is followed using the anilines of Examples 1 and 2 then the corresponding product is obtained.

When methylisothiocyanate is replaced by the isothiocyanates of Table I below, then the corresponding product is obtained.

TABLE I ethylisothiocyanate
propylisothiocyanate
i-propylisothiocyanate
butylisothiocyanate
pentylisothiocyanate
hexylisothiocyanate
heptylisothiocyanate
octylisothiocyanate
vinylisothiocyanate
propargylisothiocyanate
methallylisothiocyanate
cyclopropylisothiocyanate
cyclobutylisothiocyanate
cyclopentylisothiocyanate
cyclohexylisothiocyanate
cyclohex-2-enyliosthiocyanate
phenyliosthiocyanate
benzylisothiocyanate
phenethylisothiocyanate
cyclopropylmethylisothiocyanate
cyclobutylmethylisothiocyanate
cyclopropylethylisothiocyanate

EXAMPLE 5

1-(2,6-dichlorophenyl)-3-methylguanidine 1-(2,6-dichlorophenyl)-3-benzoylthiourea To 51.8 g. (0.68 mole) of ammonium thiocyanate in 300 ml acetone is added 86.8 g (0.62 mole) of benzoyl chloride. The reaction mixture is refluxed for about 5 min. and then 100 g (0.62 mole) of 2,6-dichloroaniline in 200 ml acetone is added at a rate to maintain reflux. The mixture is refluxed for 1½ hours, cooled, poured into 1½ liters of ice and water, filtered to obtain 1-(2,6-dichlorophenyl)-3-benzoylthiourea.

2,6-dichlorophenylthiourea 182.8 g (0.56 mole) of the latter is heated with 260 ml of 10% sodium hydroxide, filtered, acidified while hot with conc. hydrochloric acid and then made basic with conc. ammonium hydroxide. The mixture is then chilled in an ice bath and the resultant 2,6-dichlorophenylthiourea is filtered off.

1-(2,6-dichlorophenyl)-2-methylpseudothiouronium iodide 20 g (0.09 mole) of 2,6-dichlorophenylthiourea is combined with 200 ml methanol and 12.9 g (0.09 mole) iodomethane and refluxed for 4 hours. This is then evaporated to dryness and 100 ml hexane is added and the mixture filtered to botain 1-(2,6-dichlorophenyl)-2-methylpseudothiouronium iodide.

1-(2,6-dichlorophenyl)-3-methylguanidine hydrochloride 32.8 g (0.09 mole) of the latter is added to 300 ml of n-butanol. Methylamine gas is bubbled through this solution while refluxing for 24 hours. The reaction mixture is evaporated to dryness and extracted with 10% sodium hydroxide solution and ether. The ether is washed with 10% sodium hydroxide and then with water, dried and filtered. To this is added ethereal HCl and the precipitate is collected to obtain 1-(2,6-dichlorophenyl)-3-methylguanidine hydrochloride.

The free base is prepared by dissolving 1-(2,6-dichlorophenyl)-3-methylguanidine hydrochloride in 10% sodium hydroxide solution and extracting with ether. The ether is dried and evaporated to dryness to obtain 1-(2,6-dichlorophenyl)-3-methylguanidine.

When the above procedures are followed using the anilines of Examples 1 and 2, then the corresponding product is obtained.

When the above procedures are followed and methylamine is replaced with the amines of Table I below, then the corresponding product is obtained.

TABLE I ethylamine
propylamine
i-propylamine
butylamine
pentylamine
hexylamine
heptylamine
octylamine
propargylamine
methallylamine
2,4-pentadienylamine
cyclopropylamine
cyclobutylamine cyclopentylamine
cyclohexylamine
propionamide
aniline
benzylamine
phenethylamine
cyclohex-2-enylamine
cyclopropylmethylamine
cyclobutylmethylamine
cyclopropylethylamine
N-benzylaniline
azetidine
piperidine
homopiperidine
morpholine
pyrollidine
piperazine
2-methyl-1-azacyclooctane When the above procedures are followed using the anilines of Examples 1 and 2 and the amines of Table I above the corresponding products are obtained.

When the thiorea compounds prepared of Example 4 are substituted in the above procedure, then the corresponding products are obtained.

EXAMPLE 6

1-(2,6-dichlorophenylamidino)-3-(t-butyl)urea

To a mixture of 10 g (0.05 mole) of 2,6-dichlorophenylguanidine and 10 ml xylene is added 5 g of t-butylisocyanate (0.05 mole) and the mixture is refluxed for 2 hours. The reaction product is cooled, triturated with heptane and filtered. Recrystallization from 1:1 isopropanol/water results in 1-(2,6-dichlorophenylamidino)-3-(t-butyl)urea.

When the above procedure is followed using the guanidines of Example 1, then the corresponding products of Table I below are prepared.

TABLE I 1-(o-chlorophenylamidino)-3-(t-butyl)urea
1-(m-chlorophenylamidino)-3-(t-butyl)urea
1-(p-chlorophenylamidino)-3-(t-butyl)urea
1-(2,3-dichlorophenylamidino)-3-(t-butyl)urea
1-(2,4-dichlorophenylamidino)-3-(t-butyl)urea
1-(2,5-dichlorophenylamidino)-3-(t-butyl)urea
1-(3,4-dichlorophenylamidino)-3-(t-butyl)urea
1-(3,5-dichlorophenylamidino)-3-(t-butyl)urea
1-(2,3,4-trichlorophenylamidino)-3-(t-butyl)urea
1-(2,3,5-trichlorophenylamidino)-3-(t-butyl)urea
1-(2,3,6-trichlorophenylamidino)-3-(t-butyl)urea
1-(2,4,5-trichlorophenylamidino)-3-(t-butyl)urea
1-(2,4,6-trichlorophenylamidino)-3-(t-butyl)urea
1-(3,4,5-trichlorophenylamidino)-3-(t-butyl)urea
1-(o-bromophenylamidino)-3-(t-butyl)urea
1-(m-bromophenylamidino)-3-(t-butyl)urea
1-(p-bromophenylamidino)-3-(t-butyl)urea
1-(2,3-dibromophenylamidino)-3-(t-butyl)urea
1-(2,4-dibromophenylamidino)-3-(t-butyl)urea
1-(2,5-dibromophenylamidino)-3-(t-butyl)urea
1-(2,6-dibromophenylamidino)-3-(t-butyl)urea
1-(3,4-dibromophenylamidino)-3-(t-butyl)urea
1-(3,5-dibromophenylamidino)-3-(t-butyl)urea
1-(2-chloro-3-bromophenylamidino)-3-(t-butyl)urea
1-(2-chloro-4-bromophenylamidino)-3-(t-butyl)urea
1-(2-chloro-5-bromophenylamidino)-3-(t-butyl)urea
1-(2-chloro-6-bromophenylamidino)-3-(t-butyl)urea
1-(3-chloro-2-bromophenylamidino)-3-(t-butyl)urea
1-(3-chloro-4-bromophenylamidino)-3-(t-butyl)urea
1-(3-chloro-5-bromophenylamidino)-3-(t-butyl)urea
1-(3-chloro-6-bromophenylamidino)-3-(t-butyl)urea
1-(4-chloro-2-bromophenylamidino)-3-(t-butyl)urea
1-(4-chloro-3-bromophenylamidino)-3-(t-butyl)urea
1-(2-fluoro-4-chlorophenylamidino)-3-(t-butyl)urea
1-(2-fluoro-6-chlorophenylamidino)-3-(t-butyl)urea
1-(2-chloro-4-fluorophenylamidino)-3-(t-butyl)urea
1-(2-fluoro-6-bromophenylamidino)-3-(t-butyl)urea
1-(2-bromo-4-fluorophenylamidino)-3-(t-butyl)urea
1-(2-iodo-4-chlorophenylamidino)-3-(t-butyl)urea
1-(2-iodo-6-chlorophenylamidino)-3-(t-butyl)urea
1-(2-chloro-4-iodophenylamidino)-3-(t-butyl)urea
1-(2-iodo-4-bromophenylamidino)-3-(t-butyl)urea
1-(o-fluorophenylamidino)-3-(t-butyl)urea
1-(m-fluorophenylamidino)-3-(t-butyl)urea
1-(p-fluorophenylamidino)-3-(t-butyl)urea
1-(p-iodophenylamidino)-3-(t-butyl)urea
1-(2,4-difluorophenylamidino)-3-(t-butyl)urea
1-(2,5-difluorophenylamidino)-3-(t-butyl)urea
1-(2,6-difluorophenylamidino)-3-(t-butyl)urea
1-(2,4-diiodophenylamidino)-3-(t-butyl)urea
1-(2-iodo-6-bromophenylamidino)-3-(t-butyl)urea
1-(2-bromo-4-iodophenylamidino)-3-(t-butyl)urea
1-(2-fluoro-4-iodophenylamidino)-3-(t-butyl)urea
1-(2-iodo-4-fluorophenylamidino)-3-(t-butyl)urea
1-(o-trifluoromethylphenylamidino)-3-(t-butyl)urea
1-(m-trifluoromethylphenylamidino)-3-(t-butyl)urea
1-(p-trifluoromethylphenylamidino)-3-(t-butyl)urea
1-(p-trifluoromethoxyphenylamidino)-3-(t-butyl)urea
1-(p-methylsulfonylphenylamidino)-3-(t-butyl)urea
1-(1-nitrophenylamidino)-3-(t-butyl)urea
1-(m-nitrophenylamidino)-3-(t-butyl)urea
1-(p-nitrophenylamidino)-3-(t-butyl)urea
1-(2-chloro-4-nitrophenylamidino)-3-(t-butyl)urea
1-(2-bromo-4-nitrophenylamidino)-3-(t-butyl)urea
1-(2-iodo-4-nitrophenylamidino)-3-(t-butyl)urea
1-(2-fluoro-4-nitrophenylamidino)-3-(t-butyl)urea
1-(2-nitro-4-chlorophenylamidino)-3-(t-butyl)urea
1-(2-nitro-4-bromophenylamidino)-3-(t-butyl)urea
1-(2-nitro-4-fluorophenylamidino)-3-(t-butyl)urea
1-(2-nitro-4-trifluoromethylphenylamidino)-3-(t-butyl)urea
1-(2-nitro-4-methoxyphenylamidino)-3-(t-butyl)urea
1-(2-cyano-4-chlorophenylamidino)-3-(t-butyl)urea
1-(2-chloro-4-cyanophenylamidino)-3-(t-butyl)urea
1-(2-methyl-4-chlorophenylamidino)-3-(t-butyl)urea
1-(2-methyl-4-bromophenylamidino)-3-(t-butyl)urea
1-(2-trifluoromethyl-4-chlorophenylamidino)-3-(t-butyl)urea
1-(2-trifluoromethyl-4-bromophenylamidino)-3-(t-butyl)urea
1-(2-trifluoromethyl-4-fluorophenylamidino)-3-(t-butyl)urea
1-(4-trifluoromethyl-2-chlorophenylamidino)-3-(t-butyl)urea
1-(4-trifluoromethyl-2-bromophenylamidino)-3-(t-butyl)urea
1-(4-trifluoromethyl-2-fluorophenylamidino)-3-(t-butyl)urea
1-(2,4-dichloro-6-methylphenylamidino)-3-(t-butyl)urea
1-(2,6-dichloro-4-methylphenylamidino)-3-(t-butyl)urea
1-(3,5-ditrifluoromethylphenylamidino)-3-(t-butyl)urea
1-(2-methoxy-4-nitrophenylamidino)-3-(t-butyl)urea
1-(2-trifluoromethyl-4-nitrophenylamidino)-3-(t-butyl)urea 1-(2,4-dichloro-6-methoxyphenylamidino)-3-(t-butyl)urea
1-(2,6-dimethyl-4-chlorophenylamidino)-3-(t-butyl)urea
1-(2,6-dimethyl-4-fluorophenylamidino)-3-(t-butyl)urea
1-(2,6-dimethyl-4-bromophenylamidino)-3-(t-butyl)urea
1-(2,6-dimethyl-4-nitrophenylamidino)-3-(t-butyl)urea
1-(2,6-dimethyl-4-trifluoromethylphenylamidino)-3-(t-butyl)urea
1-(2-ethyl-4-nitrophenylamidino)-3-(t-butyl)urea
1-(2-ethyl-4-chlorophenylamidino)-3-(t-butyl)urea
1-(2-ethyl-4-bromophenylamidino)-3-(t-butyl)urea
1-(2-ethyl-4-fluorophenylamidino-3-(t-butyl)urea
1-(2-ethyl-4-trifluoromethylphenylamidino-3-(t-butyl)urea
1-(2-ethyl-4-cyanophenylamidino)-3-(t-butyl)urea
1-(2-ethyl-4-methylsulfonylphenylamidino)-3-(t-butyl)urea
1-(2,4-dichloro-6-bromophenylamidino)-3-(t-butyl)urea
1-(2,6-dichloro-4-bromophenylamidino)-3-(t-butyl)urea
1-(2,4-dibromo-6-chlorophenylamidino)-3-(t-butyl)urea
1-(2,6-dibromo-4-chlorophenylamidino)-3-(t-butyl)urea
1-(2,4-dichloro-6-fluorophenylamidino)-3-(t-butyl)urea
1-(2-chloro-4-methyl-6-fluorophenylamidino)-3-(t-butyl)urea
1-(2,4-dimethyl-6-chlorophenylamidino)-3-(t-butyl)urea
1-(2,4-dimethyl-6-fluorophenylamidino)-3-(t-butyl)urea
1-(2-chloro-4-fluoro-6-methylphenylamidino)-3-(t-butyl)urea
1-(2,6-dichloro-4-fluorophenylamidino)-3-(t-butyl)urea
1-(2,5-dichloro-4-fluorophenylamidino)-3-(t-butyl)urea
1-(2,4-dichloro-6-iodophenylamidino)-3-(t-butyl)urea
1-(2,6-dichloro-4-iodophenylamidino)-3-(t-butyl)urea
1-(2,4-dibromo-6-iodophenylamidino)-3-(t-butyl)urea
1-(2,4-dibromo-6-fluorophenylamidino)-3-(t-butyl)urea
1-(2,6-dibromo-4-fluorophenylamidino)-3-(t-butyl)urea
1-(2-chloro-4bromo-6-fluorophenylamidino)-3-(t-butyl)urea
1-(2-bromo-4-fluoro-6-chlorophenylamidino)-3-(t-butyl)urea
1-(2-bromo-4-chloro-6-fluorophenylamidino)-3-(t-butyl)urea
1-(2-chloro-4-iodo-6-bromophenylamidino)-3-(t-butyl)urea
1-(2,4,6-tribromophenylamidino)-3-(t-butyl)urea
1-(2,4,6-trifluorophenylamidino)-3-(t-butyl)urea When t-butylisocyanate in the above procedure is replaced by the isocyanates of Table II below, then the corresponding product is prepared.

TABLE II
methylisocyanate
ethylisocyanate
propylisocyanate
i-propylisocyanate
butylisocyanate
pentylisocyanate
hexylisocyanate
heptylisocyanate
octylisocyanate
propargylisocyanate
methallylisocyanate
cyclopropylisocyanate
cyclobutylisocyanate
cyclopentylisocyanate
cyclohexylisocyanate
cyclohex-2-enylisocyanate
phenylisocyanate
benzylisocyanate
phenethylisocyanate
cyclopropylmethylisocyanate
cyclobutylmethylisocyanate
cyclopropylethylisocyanate When the above procedure is followed using the guanidines of Examples 1 and 3 and the isocyanates of Table II above, then the corresponding product is prepared.

EXAMPLE 7

1-(2,6-dichlorophenyl-N-methylamidino)urea 1-(2,6-dichlorophenyl-N-methylamidino)-3-(t-butyl)urea To a mixture of 10.9 g (0.05 mole) of 1-(2,6-dichlorophenyl)-1-methylguanidine and 10 ml xylene is added 5 g of t-butylisocyanate (0.05 mole) and the mixture is refluxed for 2 hours. The reaction product is cooled, triturated with heptane and filtered. Recrystallization from 1:1 isopropanol/water results in 1-(2,6-dichlorophenyl-N-methylamidino)-3-(t-butyl)urea.

1-(2,6-dichlorophenyl-N-methylamidino)urea

A mixture os 33.7 g (0.106 mole) of 1-(2,6-dichlorophenyl-N-methylamidino)-3-(t-butyl)urea and 200 ml of conc. hydrochloric acid is refluxed for ½ hour. The reaction mixture is cooled, filtered and washed with 10 ml of 1:1 HCl/H$_2$O and dried. The product is then recrystallized from ethanol-ether to obtain 1-(2,6-dichlorophenyl-N-methylamidino)urea.

When the above procedure is followed using 1-(2,6-dichlorophenyl)-3-methylguanidine and 1-(2,6-dichlorophenyl)-1,3-dimethylguanidine then the products prepared are 1-(2,6-dichlorophenylamidino)-1-methylurea and 1-(2,6-dichlorophenyl-N-methylamidino)-1-methylurea.

When the above procedure is followed using the guanidines of Examples 2, 3 and 5, then the corresponding products are prepared.

EXAMPLE 8

1-(2,6-dichlorophenyl)-3-carbamylthiourea 1-(2,6-dichlorophenyl)-3-(t-butylcarbamyl)thiourea To a mixture of 11 g (0.05 mole) of 1-(2,6-dichlorophenyl)thiourea and 10 ml of xylene is added 5 g of t-butylisocyanate (0.05 mole) and the mixture is refluxed for 2 hours. The reaction product is cooled, triturated with heptane and filtered. Recrystallization from 1:1 isopropanol/water results in 1-(2,6-dichlorophenyl)-3-(t-butylcarbamyl)thiourea.

1-(2,6-dichlorophenyl)-3-carbamylthiourea

A mixture of 32 g (0.1 mole) of 1-(2,6-dichlorophenyl)-3-(t-butylcarbamyl)thiourea and 200 ml of conc. hydrochloric acid is refluxed for ½ hour. The reaction mixture is cooled, filtered and washed with 10 ml of 1:1 HCl/H$_2$O and dried. The product is then recrystallized from ethanol-ether to obtain 1-(2,6-dichlorophenyl)-3-carbamylthiourea.

When the above procedure is followed using 1-(2,6-dichlorophenyl)-1-methylthiourea; 1-(2,6-dichlorophenyl)-3-methylthiourea; 1-(2,6-dichlorophenyl)-1,3-dimethylthiourea; 1-(p-fluorophenyl)-3-methylthiourea then the products obtained are 1-(2,6-dichlorophenyl)-1-methyl-3-carbamylthiourea; 1-(2,6dichlorophenyl)-3- methyl-3-carbamylthiourea; 1-(2,6-dichlorophenyl)-1,3-dimethyl-3-carbamylthiourea; and 1-(p-fluorophenyl)-3-methyl-3-carbamylthiourea.

When the above procedure is followed using the thiourea compounds of Examples 4 and 5 then the corresponding product is obtained.

When the above procedure is followed using the substituted isocyanate compounds of Table II, Example 6, then the corresponding product is obtained.

When the above procedure is followed using the thiourea compounds of Examples 4 and 5 and the substituted isocyanate compounds of Table II, Example 6, then the corresponding product is obtained.

EXAMPLE 9

1-(2,6-dichlorophenyl-N'-methylamidino)urea 1-(2,6-dichlorophenyl)-3-carbamyl-2-methylthiouronium iodide 26.4 g (0.1 mole) of 1-(2,6-dichlorophenyl)-3-carbamylthiourea is combined with 200 ml of methanol and 14.1 g (0.1 mole) of iodomethane and refluxed for 4 hours. This is then evaporated to dryness and 100 ml of hexane is added. The mixture is filtered to obtain 1-(2,6-dichlorophenyl)-3-carbamyl-3-methylthiouronium iodide.

1-(2,6-dichlorophenyl-N'-methylamidino)urea 40.5 g of 1-(2,6-dichlorophenyl)-3-carbamyl-2-methylthiouronium iodide (0.1 mole) is added to 300 ml of n-butanol. Methylamine gas is bubbled through this solution while refluxing for 24 hours. The reaction mixture is evaporated to dryness and extracted with 10% sodium hydroxide solution and ether. The ether is washed with 10% sodium hydroxide and then with water; dried and filtered. To this is added ethereal HCl and the precipitate is collected to obtain 1-(2,6-dichlorophenyl-N'-methylamidino)urea hydrochloride.

The free base is prepared by dissolving the above hydrochloride in 10% sodium hydroxide solution and extracting with ether. The ether is dried and evaporated to dryness to obtain 1-(2,6-dichlorophenyl-N'-methylamidino)urea.

When the above procedure is followed using the thiourea compounds prepared by Example 8, then the corresponding amidinourea is prepared.

When the above procedure is followed and methylamine is replaced with the amines of Table I, Example 5, then the corresponding product is obtained.

When the above procedure is followed using the thiourea compounds prepared by Example 8 and the amines of Table I, Example 5, then the corresponding product is prepared.

EXAMPLE 10

1-(2,6-dichlorophenylamidino)-3,3-(α,α'-dimethylpentamethylene)urea

A. 2,6-dimethylpiperidinoyl chloride

To a solution of 50 g of 2,6-dimethylpiperidine in 300 ml of benzene is added 60 g of phosgene and the mixture is refluxed for 3 hours. The solid which had separated was filtered and the filtrate was concentrated and distilled under vacuum to obtain 2,6-dimethylpiperidinoyl chloride.

B.

1-(2,6-dichlorophenylamidino)-3,3-(α,α'-dimethylpentamethylene)urea

To a mixture of 20.4 g (0.1 mole) of 2,6-dichlorophenylguanidine in 250 ml of dimethylformamide is added dropwise with stirring a solution of 17.5 g (0.1 mole) of w,6-dimethylpiperidinoyl chloride in 150 ml of tetrahydrofuran. The mixture is stirred for 6 hours, poured onto ice, acidified with conc. HCl basified with sodium hydroxide and extracted with ether. The ether is washed with water and saturated sodium chloride solution and dried over magnesium sulfate. The filtered solution is evaporated to dryness to obtain 1-(2,6-dichlorophenylamidino)-3,3-(α,α'-dimethylpentamethylene)urea.

The hydrochloride salt is prepared by dissolving the above free base in ether and adding etheral hydrochloric acid. The formed hydrochloride is separated and recrystallized from acetonitrile/water/conc. HCl.

When 2,6-dimethylpiperidine is replaced in the above example by the amines of Table I below, then the corresponding product is prepared.

TABLE I piperidine
4-methylpiperidine
N-methylpiperazine
N-methylhomopiperazine
morpholine
thiazolidine
octamethyleneamine
2-methylazacyclooctane
pyrrolidine
dimethylamine
diethylamine
methylethylamine
ethylpropylamine
ethylcyclopropylamine
ethylbenzylamine
dibenzylamine
dicyclopropylamine
methylcyclobutylamine
methyl-t-butylamine
ethyl-t-butylamine
cyclopropyl-t-butylamine
methyl(cyclopropylmethyl)amine When 2,6-dichlorophenylguanidine in the above Example is replaced by the guanidines prepared in Examples 1, 2, 3 and 5, then the corresponding product is obtained.

When the above procedure is followed, and 2,6-dichlorophenylguanidine is replaced by the guanidines of Examples 1, 2, 3 and 5 and 2,6-dimethylpiperidine is replaced by the amines of Table I above, then the corresponding product is prepared.

EXAMPLE 11

1-(2,6-dichlorophenyl-N'-methylamidino)-3,3-diethylurea

A. 1-(2,6-dichlorophenyl)-3,3-diethylcarbamylthiourea

To a mixture of 11 g (0.05 mole) of 1-(2,6-dichlorophenyl)thiourea in 150 ml of dimethylformamide is added dropwise with stirring a solution of 6.75 g (0.01 mole) of diethylcarbamyl chloride in 100 ml of tetrahydrofuran (prepared from diethylamine and phosgene according to Example 10). The mixture is stirred for 10 hours, poured onto ice, acidified with conc. HCl while keeping the mixture at ice temperature and basified with sodium hydroxide and extracted with ether. The ether is washed, dried and evaporated to obtain 1-(2,6-dichlorophenyl)-3,3-diethylcarbamylthiourea.

B.

1-(2,6-dichlorophenyl)-3-(N,N-diethylcarbamyl)-2-methylthiouronium iodide (0.1 mole) of 1-(2,6-dichlorophenyl)-3-(N,N-diethylcarbamyl)thiourea is combined with 200 ml of methanol and 14.1 g (0.1 mole) of iodomethane and refluxed for 4 hours. This is then evaporated to dryness and 100 ml of hexane is added. The mixture is filtered to obtain 1-(2,6-dichlorophenyl)-3-(N,N-diethylcarbamyl)-2-methylthiouronium iodide.

C.

1-(2,6-dichlorophenyl)-N'-methylamidino)-3,3-diethylurea of 1-(2,6-dichlorophenyl)-3-(N,N-diethylcarbamyl)-2-methylthiouronium iodide (0.1 mole) is added to 300 ml of n-butanol. Methylamine gas is bubbled through this solution while refluxing for 24 hours. The reaction mixture is evaporated to dryness and extracted with 10% sodium hydroxide solution and ether. The ether is washed with 10% sodium hydroxide and then with water; dried filtered and evaporated to dryness to obtain 1-(2,6-dichlorophenyl-N'-methylamidino)-3,3-diethylurea.

The hydrochloride salt is prepared by dissolving the above free base in ether and adding ethereal hydrochloric acid. The formed hydrochloride is separated and recrystallized from acetonitrile/water conc. HCl.

When diethylamine is replaced in the above example by the amines of Table I, Example 10, then the corresponding product is obtained.

When 1-(2,6-dichlorophenyl)thiourea is replaced with the thioureas prepared in Examples 4 and 5 then the corresponding product is obtained.

When 1-(2,6-dichlorophenyl)thiourea is replaced with the thioureas of Examples 4 and 5 and diethylamine is replaced by the amines of Table I, Example 10, then the corresponding product is obtained.

EXAMPLE 12

Following the procedures of Examples 1–11, the following representative compounds may be prepared to demonstrate this invention.

| Starting Materials | Products | Example |
|---|---|---|
| 2,6-dichlorophenylguanidine + methylisocyanate | 1-(2,6-dichlorophenylamidino)-3-methylurea | 6 |
| 2,6-dichlorophenylguanidine + ethylisocyanate | 1-(2,6-dichlorophenylamidino)-3-ethylurea | 6 |
| 2,6-dichlorophenylguanidine + propylisocyanate | 1-(2,6-dichlorophenylamidino)-3-propylurea | 6 |
| 2,6-dichlorophenylguanidine + i-propylisocyanate | 1-(2,6-dichlorophenylamidino)-3-i-propylurea | 6 |
| 2,6-dichlorophenylguanidine + butylisocyanate | 1-(2,6-dichlorophenylamidino)-3-butylurea | 6 |
| 2,6-dichlorophenylguanidine + pentylisocyanate | 1-(2,6-dichlorophenylamidino)-3-pentylurea | 6 |
| 2,6-dichlorophenylguanidine + hexylisocyanate | 1-(2,6-dichlorophenylamidino)-3-hexylurea | 6 |
| 2,6-dichlorophenylguanidine + heptylisocyanate | 1-(2,6-dichlorophenylamidino)-3-heptylurea | 6 |
| 2,6-dichlorophenylguanidine + octylisocyanate | 1-(2,6-dichlorophenylamidino)-3-octylurea | 6 |
| 2,6-dichlorophenylguanidine + allyl isocyanate | 1-(2,6-dichlorophenylamidino)-3-allylurea | 6 |
| 2,6-dichlorophenylguanidine + propargylisocyanate | 1-(2,6-dichlorophenylamidino)-3-propargylurea | 6 |
| 2,6-dichlorophenylguanidine + methallylisocyanate | 1-(2,6-dichlorophenylamidino)-3-methallylurea | 6 |
| 2,6-dichlorophenylguanidine + cyclopropylisocyanate | 1-(2,6-dichlorophenylamidino)-3-cyclopropylurea | 6 |
| 2,6-dichlorophenylguanidine + cyclobutylisocyanate | 1-(2,6-dichlorophenylamidino)-3-cyclobutylurea | 6 |
| 2,6-dichlorophenylguanidine + cyclopentylisocyanate | 1-(2,6-dichlorophenylamidino)-3-cyclopentylurea | 6 |
| 2,6-dichlorophenylguanidine − cyclohexylisocyanate | 1-(2,6-dichlorophenylamidino)-3-cyclohexylurea | 6 |
| 2,6-dichlorophenylguanidine + (cyclohex-2-enyl)-isocyanate | 1-(2,6-dichlorophenylamidino)-3-(cyclohex-2-enyl)urea | 6 |
| 2,6-dichlorophenylguanidine + phenylisocyanate | 1-(2,6-dichlorophenylamidino)-3-phenylurea | 6 |
| 2,6-dichlorophenylguanidine + benzylisocyanate | 1-(2,6-dichlorophenylamidino)-3-benzylurea | 6 |
| 2,6-dichlorophenylguanidine + phenethylisocyanate | 1-(2,6-dichlorophenylamidino)-3-phenethylurea | 6 |
| 2,6-dichlorophenylguanidine + cyclopropylmethyl-isocyanate | 1-(2,6-dichlorophenylamidino)-3-cyclopropylmethylurea | 6 |
| 2,6-dichlorophenylguanidine + cyclobutylmethyl-isocyanate | 1-(2,6-dichlorophenylamidino)-3-cyclobutylmethylurea | 6 |
| 2,6-dichlorophenylguanidine + cyclopropylethyl-isocyanate | 1-(2,6-dichlorophenylamidino)-3-cyclopropylethylurea | 6 |
| 2,6-dichlorophenylguanidine + piperidinoyl chloride | 1-(2,6-dichlorophenylamidino)-3,3-pentamethyleneurea | 10 |
| 2,6-dichlorophenylguanidine + 4-methylpiperidinoyl chloride | 1-(2,6-dichlorophenylamidino)-3,3-γ-methylpentamethyleneurea | 10 |
| 2,6-dichlorophenylguanidine + N—methylpiperazinoyl chloride | 1-(2,6-dichlorophenylamidino)-3,3-(N—methyl-3'-azapentamethylene)urea | 10 |
| 2,6-dichlorophenylguanidine + N—methyl-homopiperazinoyl chloride | 1-(2,6-dichlorophenylamidino)-3,3-(N—methyl-3'-azahescamethylene)urea | 10 |
| 2,6-dichlorophenylguanidine + morpholinoyl chloride | 1-(2,6-dichlorophenylamidino)-3,3-(3'-oscapentamethylene)urea | 10 |
| 2,6-dichlorophenylguanidine + thiazolidinoyl chloride | 1-(2,6-dichlorophenylamidino)-3,3-(2'-thiatetramethylene)urea | 10 |
| 2,6-dichlorophenylguanidine + N,N—octamethylenecarbamyl chloride | 1-(2,6-dichlorophenylamidino)-3,3-octamethyleneurea | 10 |
| 2,6-dichlorophenylguanidine + 2-methyl-N,N—octamethylenecarbamyl chloride | 1-(2,6-dichlorophenylamidino)-3,3-α-methyloctamethyleneurea | 10 |
| 2,6-dichlorophenylguanidine + pyrrolidinoyl chloride | 1-(2,6-dichlorophenylamidino)-3,3-tetramethyleneurea | 10 |
| 2,6-dichlorophenylguanidine + N,N—dimethylcarbamyl chloride | 1-(2,6-dichlorophenylamidino)-3,3-dimethylurea | 10 |
| 2,6-dichlorophenylguanidine + N,N—diethylcarbamyl chloride | 1-(2,6-dichlorophenylamidino)-3,3-diethylurea | 10 |
| 2,6-dichlorophenylguanidine + N—ethyl-N—methylcarbamyl chloride | 1-(2,6-dichlorophenylamidino)-3-ethyl-3-methylurea | 10 |
| 2,6-dichlorophenylguanidine + N—ethyl-N— | 1-(2,6-dichlorophenylamidino)-3-ethyl-3-propylurea | 10 |

-continued

| Starting Materials | Products | Example |
|---|---|---|
| propylcarbamyl chloride | | |
| 2,6-dichlorophenylguanidine + N—cyclopropyl-N—ethylcarbamyl chloride | 1-(2,6-dichlorophenylamidino)-3-cyclopropyl-3-ethylurea | 10 |
| 2,6-dichlorophenylguanidine + N—benzyl-N—ethylcarbamyl chloride | 1-(2,6-dichlorophenylamidino)-3-benzyl-3-ethylurea | 10 |
| 2,6-dichlorophenylguanidine + N,N—dibenzylcarbamyl chloride | 1-(2,6-dichlorophenylamidino)-3,3-dibenzylurea | 10 |
| 2,6-dichlorophenylguanidine + N,N—dicyclopropylcarbamyl chloride | 1-(2,6-dichlorophenylamidino)-3,3-dicyclopropylurea | 10 |
| 2,6-dichlorophenylguanidine + N—cyclobutyl-N—methylcarbamyl chloride | 1-(2,6-dichlorophenylamidino)-3-cyclobutyl-3-methyl | 10 |
| 1-(2,6-dichlorophenyl)-1-methylguanidine + methylisocyanate | 1-(2,6-dichlorophenyl-N—methylamidino)-3-methylurea | 7 |
| 1-(2,6-dichlorophenyl)-3-(N—methylcarbamyl)-2-methylthiouronium iodide + methylamine | 1-(2,6-dichlorophenyl-N'—methylamidino)-3-methylurea | 9 |
| 1-(2,6-dichlorophenyl)-3-(N—t-butylcarbamyl)-2-methylthiouronium iodide + methylamine | 1-(2,6-dichlorophenyl-N'—methylamidino)-3-t-butylurea | 9 |
| 1-(2,6-dichlorophenyl)-3-methylguanidine + methylisocyanate | 1-(2,6-dichlorophenylamidino)-1,3-dimethylurea | 6 |
| 1-(2,6-dichlorophenyl)-3-methylguanidine + t-butylisocyanate | 1-(2,6-dichlorophenylamidino)-1-methyl-3-t-butylurea | 6 |
| 1-(2,6-dichlorophenyl)-1,3-dimethylguanidine + t-butylisocyanate | 1-(2,6-dichlorophenyl-N—methylamidino)-1-methyl-3-t-butylurea | 6 |
| 1-(2,6-dichlorophenyl)-3-methyl-3-(N—t-butylcarbamyl)-2-methyl-thiouronium iodide) + methylamine | 1-(2,6-dichlorophenyl-N'—methylamidino)-1-methyl-3-t-butylurea | 9 |
| 1-(2,6-dichlorophenyl)-1,3-dimethyl-3-(N—t-butylcarbamyl)-2-methylthiouronium iodide) + methylamine | 1-(2,6-dichlorophenyl-N,N'—dimethylamidino)-1-methyl-3-t-butylurea | 9 |
| 1-(2,6-dichlorophenyl)-1,3-dimethyl-3-(N—methylcarbamyl)-2-methylthiouronium iodide) + methylamine | 1-(2,6-dichlorophenyl-N,N'—dimethylamidino)-1,3-dimethylurea | 9 |
| p-fluorophenylguanidine + methylisocyanate | 1-(p-fluorophenylamidino)-3-methylurea | 6 |
| 1-(p-fluorophenyl)-1-methylguanidine + t-butylisocyanate | 1-(p-fluorophenyl-N—methylamidino)-3-(t-butyl)urea | 7 |
| 1-(p-fluorophenyl-N—methylamidino)-3-(t-butyl)urea + conc. HCl | 1-(p-fluorophenyl-N—methylamidino)urea | 7 |
| 1-(p-fluorophenyl)-3-methylguanidine + t-butylisocyanate | 1-(p-fluorophenyl)-1-methyl-3-(t-butyl)urea | 7 |
| 1-(p-fluorophenyl)-1,3-dimethylguanidine + t-butylisocyanate | 1-(p-fluorophenyl-N—methylamidino)-1-methyl-3-(t-butyl)urea | 7 |
| 1-(p-fluorophenylamidino)-1-methyl-3-(t-butyl)urea | 1-(p-fluorophenylamidino)-1-methylurea | 7 |
| 1-(p-fluorophenyl-N—methylamidino)-1-methyl-3-(t-butyl)urea + HCl | 1-(p-fluorophenyl-N—methylamidino)-1-methylurea | 7 |
| 1-(p-fluorophenyl)-3-carbamyl-2-methylthiouronium iodide + methylamine | 1-(p-fluorophenyl-N'—methylamidino)urea | 9 |
| p-fluorophenylguanidine + 2,6-dimethylpiperidinoyl chloride | 1-(p-fluorophenylamidino)-3,3-($\alpha,\alpha'$-dimethylpentamethylene)urea | 10 |
| 1-(p-fluorophenyl)-3-(N,N—diethylcarbamyl)-2-methylthiouronium iodide + methylamine | 1-(p-fluorophenyl-N'—methylamidino)-3,3-diethylurea | 11 |
| 1-(p-fluorophenyl)-1-methylguanidine + methylisocyanate | 1-(p-fluorophenyl-N—methylamidino)-3-methylurea | 7 |
| 1-(p-fluorophenyl)-3-(N—methylcarbamyl)-2-methylthiouronium iodide + methylamine | 1-(p-fluorophenyl-N'—methylamidino)-3-methylurea | 9 |
| 1-(p-fluorophenyl)-3-methylguanidine + methylisocyanate | 1-(p-fluorophenylamidino)-1,3-dimethylurea | 6 |
| 1-(p-fluorophenyl)-3-methyl-3-(N—methylcarbamyl)-2-methylthiouronium iodide + methylamine | 1-(p-fluorophenyl-N'—methylamidino)-1,3-dimethylurea | 9 |
| 1-(p-fluorophenyl)-1,3-dimethylguanidine + methylisocyanate | 1-(p-fluorophenyl-N—methylamidino)-1,3-dimethylurea | 6 |
| 1-(p-fluorophenyl)-1,3-dimethyl-3-(N—methylcarbamyl)-2-methylthiouronium iodide + methylamine | 1-(p-fluorophenyl-N,N'—dimethylamidino)-1,3-dimethylurea | 9 |
| p-(chlorophenylguanidine + piperidinoyl chloride | 1-(p-chlorophenylamidino)-3,3-(pentamethylene)urea | 10 |
| 1-(2,4-dichlorophenyl-N—methylamidino-3-t-butyl)urea + conc. HCl | 1-(2,4-dichlorophenyl-N—methylamidino)-urea | 7 |
| 1-(p-bromophenyl)-3-methyl-3-carbamyl-2-methylthiouronium iodide + methylamine | 1-(p-bromophenyl-N'—methylamidino)-1-methylurea | 9 |
| 1-(2-chloro-6-fluorophenyl)guanidine + ethylisocyanate | 1-(2,chloro-6-fluorophenylamidino)-3-ethylurea | 7 |
| 1-(p-trifluoromethylphenylamidino)-1-methyl-3-(t-butyl)urea + conc. HCl | 1-(p-trifluoromethylphenylamidino)-1-methylurea | 7 |
| p-trifluoromethylphenylguanidine + methylisocyanate | 1-(p-trifluoromethylphenylamidino)-3-methylurea | 6 |
| p-trifluoromethylphenylguanidine + morpholinoyl chloride | 1-(p-trifluoromethylphenylamidino)-3,3-(3'-oxapentamethylene)urea | 10 |
| 1-(p-trifluoromethoxyphenyl-N—ethylamidino)-3-(t-butyl)urea + conc. HCl | 1-(p-trifluoromethoxyphenyl-N—ethylamidino)urea | 7 |
| p-methylsulfonylphenylguanidine + N,N—diethylcarbamyl chloride | 1-(p-methylsulfonylphenylamidino)-3,3-diethylurea | 10 |
| p-nitrophenylguanidine + ethylisocyanate | 1-(p-nitrophenyl)-3-ethylurea | 6 |

| Starting Materials | Products | Example |
|---|---|---|
| 1-(2-chloro-4-cyanophenylamidino)-1-ethyl-3-t-butylurea + conc. HCl | 1-(2-chloro-4-cyanophenylamidino)-1-ethylurea | 7 |
| 1-(2-nitro-4-methoxyamidino)-1-ethyl-3-t-butylurea + conc. HCl | 1-(2-nitro-4-methoxyphenylamidino)-1-ethylurea | 7 |
| 1-(2-methyl-4-chlorophenyl-N—methylamidino)-3-t-butylurea + conc. HCl | 1-(2-methyl-4-chlorophenyl-N—methylamidino)urea | 7 |
| 1-(2-methyl-4-bromophenyl-N—methylamidino)-3-t-butylurea + conc. HCl | 1-(2-methyl-4-bromophenyl-N—methylamidino)urea | 7 |
| 1-(2-methyl-4-fluorophenyl-N—methylamidino)-3-t-butylurea + conc. HCl | 1-(2-methyl-4-fluorophenyl-N—methylamidino)urea | 7 |
| 1-(2-chloro-4-methylphenyl-N—methylamidino)-3-t-butylurea + conc. HCl | 1-(2-chloro-4-methylphenyl-N—methylamidino)urea | 7 |
| 1-(2-fluoro-4-methylphenyl-N—methylamidino)-3-t-butylurea + conc. HCl | 1-(2-fluoro-4-methylphenyl-N—methylamidino)urea | 7 |
| 1-(2-methyl-4-nitrophenyl-N—methylamidino)-3-t-butylurea + conc. HCl | 1-(2-methyl-4-nitrophenyl-N—methylamidino)urea | 7 |
| 1-(2-methyl-6-chlorophenyl-N—methylamidino)-3-t-butylurea + conc. HCl | 1-(2-methyl-6-chlorophenyl-N—methylamidino)urea | 7 |
| 1-(2-methyl-6-fluorophenyl-N—methylamidino)-3-t-butylurea + conc. HCl | 1-(2-methyl-6-fluorophenyl-N—methylamidino)urea | 7 |
| 1-(2,4-dimethylphenyl-N—methylamidino)-3-t-butylurea + conc. HCl | 1-(2,4-dimethylphenyl-N—methylamidino)urea | 7 |
| 1-(2,6-dimethylphenyl-N—methylamidino)-3-t-butylurea + conc. HCl | 1-(2,6-dimethylphenyl-N—methylamidino)urea | 7 |
| 1-(2-trifluoromethyl-4-chlorophenyl-N—methylamidino)-3-t-butylurea + conc. HCl | 1-(2-trifluoromethyl-4-chlorophenyl-N—methylamidino)urea | 7 |
| 1-(2-methyl-4-trifluoromethylphenyl-N—methylamidino)-3-t-butylurea + conc. HCl | 1-(2-methyl-4-trifluoromethylyphenyl-N—methylamidino)urea | 7 |
| 1-(2,4-dichloro-6-methylphenyl-N—methylamidino)-3-t-butylurea + conc. HCl | 1-(2,4-dichloro-6-methylphenyl-N—methylamidino)urea | 7 |
| 1-(2,6-dichloro-4-methylphenyl-N—methylamidino)-3-t-butylurea + conc. HCl | 1-(2,6-dichloro-4-methylphenyl-N—methylamidino)urea | 7 |
| 1-(2-chloro-4-methyl-6-fluorophenyl-N—methylamidino)-3-t-butylurea + conc. HCl | 1-(2-chloro-4-methyl-6-fluorophenyl-N— methylamidino)urea | 7 |
| 1-(2,6-dimethyl-4-chlorophenyl-N—methylamidino)-3-t-butylurea + conc. HCl | 1-(2,6-dimethyl-4-chlorophenyl-N—methylamidino)urea | 7 |
| 1-(2,6-dimethyl-4-fluorophenyl-N—methylamidino)-3-t-butylurea + conc. HCl | 1-(2,6-dimethyl-4-fluorophenyl-N—methylamidino)urea | 7 |
| 1-(2,4,6-trichlorophenyl-N—methylamidino)-3-t-butylurea + conc. HCl | 1-(2,4,6-trichlorophenyl-N—methylamidino)urea | 7 |
| 1-(2-chloro-4-methyl-6-fluorophenyl-N—methylamidino)-3-t-butylurea + conc. HCl | 1-(2-chloro-4-methyl-6-fluorophenyl-N—methylamidino)urea | 7 |
| 1-(2,4-dimethyl-6-chlorophenyl-N—methylamidino)-3-t-butylurea + conc. HCl | 1-(2,4-dimethyl-6-chlorophenyl-N—methylamidino)urea | 7 |
| 1-(2,4-dimethyl-6-fluorophenyl-N—methylamidino)-3-t-butylurea + conc. HCl | 1-(2,4-dimethyl-6-fluorophenyl-N—methylamidino)urea | 7 |
| 1-(2-chloro-4-fluoro-6-methylphenyl-N—methylamidino)-3-t-butylurea + conc. HCl | 1-(2-chloro-4-fluoro-6-methylphenyl-N—methylamidino)urea | 7 |
| 1-(2,6-dichloro-4-fluorophenyl-N—methylamidino)-3-t-butylurea + conc. HCl | 1-(2,6-dichloro-4-fluorophenyl-N—methylamidino)urea | 7 |
| 2-methyl-4-chlorophenylguanidine + piperidinoyl chloride | 1-(2-methyl-4-chlorophenylamidino)-3,3-pentamethyleneurea | 10 |
| 2-methyl-4-chlorophenyl-3-methylguanidine + methylisocyanate | 1-(2-methyl-4-chlorophenylamidino)-1,3-dimethylurea | 6 |
| 2-chloro-4-methylphenyl-3-methylguanidine + methylisocyanate | 1-(2-chloro-4-methylphenylamidino)-1,3-dimethylurea | 6 |
| 2-methyl-6-chlorophenyl-3-methylguanidine + methylisocyanate | 1-(2-methyl-6-chlorophenylamidino)-1,3-dimethylurea | 6 |
| 1-(2,4,6-trichlorophenyl-1,2,3-trimethyl-3-(N,N—pentamethylenecarbamyl)thiouronium iodide + methylamine | 1-(2,4,6-trichlorophenyl-N,N'—dimethylamidino)-1-methyl-3,3-pentamethyleneurea | 9 |

We claim:
1. A compound of the formula

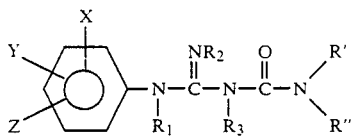

where:
- X is in the 6-position and is, halo;
- Y is in the 4-position and is halo, or loweralkyl;
- Z is in the 2-position and is halo;
- $R_1$, $R_2$ and $R_3$ are hydrogen or loweralkyl;
- R' and R" are hydrogen, loweralkenyl, cycloalkyl, cycloalkylloweralkyl, aralkyl, cycloalkenyl or
- R' and R" together are loweralkylidenyl or heteroloweralkylidenyl, provided $R_1$, $R_2$, $R_3$, R' and R" are not all hydrogen at the same time; and the non-toxic acid addition salts thereof.

2. A compound according to claim 1 where:
- X is in the 6-position and is chloro, bromo or fluoro;
- Y is in the 4-position and is methyl, ethyl, chloro, bromo or fluoro; and
- Z is in the 2-position and is chloro, bromo or fluoro.

* * * * *